US009265887B2

(12) United States Patent
Julian et al.

(10) Patent No.: US 9,265,887 B2
(45) Date of Patent: Feb. 23, 2016

(54) AUTOMATIC INJECTION DEVICES HAVING OVERMOLDED GRIPPING SURFACES

(75) Inventors: Joseph F. Julian, Libertyville, IL (US); Chuan Li, Deerfield, IL (US); Aaron B. Eiger, Chicago, IL (US); Mark Kurth, Beverly Shores, IN (US); Sabrina Katz, Chicago, IL (US); Adam Callif, Chicago, IL (US); James C. Stango, West Chester, PA (US)

(73) Assignee: AbbVie Biotechnology Ltd., Hamilton (BM)

(*) Notice: Subject to any disclaimer, the term of this patent is extended or adjusted under 35 U.S.C. 154(b) by 0 days.

(21) Appl. No.: 13/357,507

(22) Filed: Jan. 24, 2012

(65) Prior Publication Data
US 2012/0289905 A1 Nov. 15, 2012

Related U.S. Application Data

(60) Provisional application No. 61/435,465, filed on Jan. 24, 2011.

(51) Int. Cl.
A61M 5/31 (2006.01)
A61M 5/32 (2006.01)
(Continued)

(52) U.S. Cl.
CPC ............. A61M 5/20 (2013.01); A61M 5/3137 (2013.01); A61B 5/150259 (2013.01);
(Continued)

(58) Field of Classification Search
CPC ............ A61B 5/150259; A61B 5/150274; A61B 5/150282; A61B 5/150297; A61M 2005/206; A61M 2205/586; A61M 2207/00; A61M 5/20; A61M 5/3137

USPC ............. 604/68–72, 181, 183–184, 187–188, 604/192–199, 110, 171, 243, 263; 128/919; 29/428; 427/402
See application file for complete search history.

(56) References Cited

U.S. PATENT DOCUMENTS 2,398,544 A 4/1946 Lockhart
2,459,875 A 1/1949 Folkman
(Continued)

FOREIGN PATENT DOCUMENTS

DE 2019296 11/1971
DE 19821933 11/1999
(Continued)

OTHER PUBLICATIONS

Communication pursuant to Article 94(3) EPC issued by the European Patent Office in European Application No. 05758156.3-2320, dated Jan. 18, 2011.
(Continued)

Primary Examiner — Quynh-Nhu H Vu
(74) Attorney, Agent, or Firm — McCarter & English, LLP; David R. Burns

(57) ABSTRACT

Exemplary embodiments provide automatic injection devices, housing components for automatic injection devices and methods for fabricating the same. An exemplary housing of an automatic injection device may be overmolded with one or more gripping surfaces to facilitate gripping and manipulation of the automatic injection device by a user when performing an injection. In an exemplary embodiment, an overmolded left gripping surface may extend along a left side of the housing and an overmolded right gripping surface may extend along a right side of the housing opposite to the left side.

38 Claims, 8 Drawing Sheets

(51) Int. Cl.
*B23P 17/04* (2006.01)
*B05D 1/36* (2006.01)
*A61M 5/20* (2006.01)
*A61B 5/15* (2006.01)
*A61M 5/315* (2006.01)

(52) U.S. Cl.
CPC ........ *A61B 5/150274* (2013.01); *A61M 5/3157* (2013.01); *A61M 5/3202* (2013.01); *A61M 2005/206* (2013.01); *A61M 2005/3125* (2013.01); *A61M 2205/584* (2013.01); *A61M 2205/586* (2013.01); *A61M 2207/00* (2013.01); *Y10T 29/49826* (2015.01)

(56) References Cited

U.S. PATENT DOCUMENTS

| | | |
|---|---|---|
| 2,565,081 A | 8/1951 | Maynes |
| 2,591,457 A | 4/1952 | Maynes |
| 2,701,566 A | 2/1955 | Krug |
| 2,752,918 A | 7/1956 | Uytenbogaart |
| 2,832,339 A | 4/1958 | Sarnoff et al. |
| 2,888,924 A | 6/1959 | Dunmire |
| 2,960,087 A | 11/1960 | Uytenbogaart |
| 3,051,173 A | 8/1962 | Johnson et al. |
| 3,055,362 A | 9/1962 | Uytenbogaart |
| 3,066,670 A | 12/1962 | Stauffer |
| 3,136,313 A | 6/1964 | Enstrom et al. |
| 3,314,428 A | 4/1967 | Johnson et al. |
| 3,330,279 A | 7/1967 | Sarnoff et al. |
| 3,403,680 A | 10/1968 | Sinclair et al. |
| 3,543,603 A | 12/1970 | Gley |
| 3,605,743 A | 9/1971 | Arce |
| 3,618,603 A | 11/1971 | Levenson |
| 3,656,472 A * | 4/1972 | Ben Moura .......... A61B 5/1405 600/576 |
| 3,702,609 A | 11/1972 | Steiner |
| 3,712,301 A | 1/1973 | Sarnoff |
| 3,742,948 A | 7/1973 | Post |
| 3,797,488 A | 3/1974 | Hurschman et al. |
| 3,797,489 A | 3/1974 | Sarnoff |
| 3,882,863 A | 5/1975 | Sarnoff et al. |
| 3,892,237 A | 7/1975 | Steiner |
| 3,910,260 A | 10/1975 | Sarnoff et al. |
| 3,941,130 A | 3/1976 | Tibbs |
| 4,004,577 A | 1/1977 | Sarnoff |
| 4,031,893 A | 6/1977 | Kaplan et al. |
| 4,106,770 A | 8/1978 | Gray |
| 4,178,928 A | 12/1979 | Tischlinger |
| 4,202,314 A | 5/1980 | Smirnov et al. |
| 4,214,584 A | 7/1980 | Smirnov et al. |
| 4,226,235 A | 10/1980 | Sarnoff et al. |
| 4,258,713 A | 3/1981 | Wardlow |
| 4,261,358 A | 4/1981 | Vargas et al. |
| 4,275,729 A | 6/1981 | Silver et al. |
| 4,394,863 A | 7/1983 | Bartner |
| 4,425,120 A | 1/1984 | Sampson et al. |
| 4,437,859 A | 3/1984 | Whitehouse et al. |
| 4,447,231 A | 5/1984 | Bekkering |
| 4,530,695 A | 7/1985 | Phillips et al. |
| 4,565,543 A | 1/1986 | Bekkering et al. |
| 4,573,976 A | 3/1986 | Sampson et al. |
| 4,578,064 A | 3/1986 | Sarnoff et al. |
| 4,624,660 A | 11/1986 | Mijers et al. |
| 4,637,403 A | 1/1987 | Garcia et al. |
| 4,664,653 A | 5/1987 | Sagstetter et al. |
| 4,678,461 A | 7/1987 | Mesa |
| 4,689,042 A | 8/1987 | Sarnoff et al. |
| 4,723,937 A | 2/1988 | Sarnoff et al. |
| 4,755,169 A | 7/1988 | Sarnoff et al. |
| 4,795,432 A | 1/1989 | Karczmer |
| 4,795,433 A | 1/1989 | Sarnoff |
| 4,820,286 A | 4/1989 | van der Wal |
| 4,822,340 A | 4/1989 | Kamstra |
| 4,850,994 A | 7/1989 | Zerbs et al. |
| 4,852,768 A | 8/1989 | Bartsch |
| 4,902,279 A | 2/1990 | Schmidtz et al. |
| 4,923,447 A | 5/1990 | Morgan |
| 4,927,416 A | 5/1990 | Tomkiel |
| 4,929,237 A | 5/1990 | Medway |
| 4,955,868 A | 9/1990 | Klein |
| 4,966,592 A | 10/1990 | Burns et al. |
| 4,994,034 A | 2/1991 | Botich et al. |
| 5,041,088 A | 8/1991 | Ritson et al. |
| 5,042,977 A | 8/1991 | Bechtold et al. |
| 5,049,133 A | 9/1991 | Villen Pascual |
| D322,479 S | 12/1991 | Miyaguchi |
| 5,085,641 A | 2/1992 | Sarnoff et al. |
| 5,085,642 A | 2/1992 | Sarnoff et al. |
| 5,092,842 A | 3/1992 | Bechtold et al. |
| 5,092,843 A | 3/1992 | Monroe et al. |
| 5,102,393 A | 4/1992 | Sarnoff et al. |
| 5,104,380 A | 4/1992 | Holman et al. |
| 5,114,406 A | 5/1992 | Gabriel et al. |
| 5,114,410 A | 5/1992 | Caralt Battle |
| 5,137,516 A | 8/1992 | Rand et al. |
| 5,163,918 A | 11/1992 | Righi |
| 5,201,708 A | 4/1993 | Martin |
| 5,224,936 A | 7/1993 | Gallagher |
| 5,242,240 A | 9/1993 | Gorham |
| 5,244,465 A | 9/1993 | Michel |
| 5,259,840 A | 11/1993 | Boris |
| 5,263,934 A | 11/1993 | Haak |
| 5,267,963 A | 12/1993 | Bachynsky |
| 5,267,972 A | 12/1993 | Anderson |
| 5,267,976 A | 12/1993 | Guerineau et al. |
| 5,273,544 A | 12/1993 | van der Wal |
| D343,897 S | 2/1994 | Rand et al. |
| 5,295,965 A | 3/1994 | Wilmot |
| 5,295,975 A | 3/1994 | Lockwood |
| 5,298,024 A | 3/1994 | Richmond |
| D346,219 S | 4/1994 | Fardigh |
| 5,300,030 A | 4/1994 | Crossman |
| 5,318,538 A | 6/1994 | Martin |
| 5,320,609 A | 6/1994 | Haber et al. |
| 5,334,144 A | 8/1994 | Alchas et al. |
| 5,342,308 A | 8/1994 | Boschetti |
| 5,346,480 A | 9/1994 | Hess |
| 5,358,489 A | 10/1994 | Wyrick |
| 5,376,080 A | 12/1994 | Petrussa |
| 5,378,233 A | 1/1995 | Haber et al. |
| 5,383,865 A | 1/1995 | Michel |
| 5,391,151 A | 2/1995 | Wilmot |
| 5,425,715 A | 6/1995 | Dalling et al. |
| 5,433,712 A | 7/1995 | Stiles |
| 5,478,316 A | 12/1995 | Bitdinger et al. |
| 5,480,387 A | 1/1996 | Gabriel et al. |
| 5,531,705 A | 7/1996 | Alter et al. |
| 5,569,192 A | 10/1996 | van der Wal |
| 5,591,138 A | 1/1997 | Vaillancourt |
| 5,599,309 A | 2/1997 | Marshall et al. |
| 5,616,128 A | 4/1997 | Meyer |
| 5,620,421 A | 4/1997 | Schmitz |
| 5,634,906 A | 6/1997 | Haber et al. |
| 5,637,094 A | 6/1997 | Stewart, Jr. et al. |
| 5,645,534 A | 7/1997 | Chanoch |
| 5,658,259 A | 8/1997 | Pearson et al. |
| 5,681,291 A | 10/1997 | Galli |
| 5,744,360 A | 4/1998 | Hu et al. |
| 5,779,677 A | 7/1998 | Frezza |
| 5,807,335 A | 9/1998 | Kriesel et al. |
| 5,807,346 A | 9/1998 | Frezza |
| 5,817,111 A | 10/1998 | Riza |
| 5,843,036 A | 12/1998 | Olive et al. |
| 5,885,250 A | 3/1999 | Kriesel et al. |
| 5,931,817 A | 8/1999 | Nguyen et al. |
| 5,957,886 A | 9/1999 | Weston |
| 5,957,897 A | 9/1999 | Jeffrey |
| 5,984,900 A | 11/1999 | Mikkelsen |
| 5,993,421 A | 11/1999 | Kriesel |
| 6,048,336 A | 4/2000 | Gabriel |
| 6,056,728 A | 5/2000 | von Schuckmann |
| 6,077,247 A | 6/2000 | Marshall et al. |
| 6,090,070 A | 7/2000 | Hager et al. |

(56) References Cited

U.S. PATENT DOCUMENTS

| | | | |
|---|---|---|---|
| 6,090,080 A | 7/2000 | Jost et al. | |
| 6,090,382 A | 7/2000 | Salfeld et al. | |
| 6,099,503 A | 8/2000 | Stradella | |
| 6,102,896 A | 8/2000 | Roser | |
| 6,110,147 A | 8/2000 | Perouse | |
| 6,149,626 A | 11/2000 | Bachynsky et al. | |
| 6,159,181 A | 12/2000 | Crossman et al. | |
| 6,171,285 B1 | 1/2001 | Johnson | |
| 6,203,530 B1 | 3/2001 | Stewart, Sr. | |
| 6,210,369 B1 | 4/2001 | Wilmot et al. | |
| 6,213,987 B1 | 4/2001 | Hirsch | |
| 6,221,044 B1 | 4/2001 | Greco | |
| 6,241,709 B1 | 6/2001 | Bechtold et al. | |
| 6,258,068 B1 | 7/2001 | Kirchofer et al. | |
| 6,258,562 B1 | 7/2001 | Salfeld et al. | |
| 6,270,479 B1 | 8/2001 | Bergens et al. | |
| 6,277,097 B1 | 8/2001 | Mikkelsen et al. | |
| 6,277,098 B1 | 8/2001 | Klitmose et al. | |
| 6,277,099 B1 | 8/2001 | Strowe et al. | |
| 6,280,421 B1 | 8/2001 | Kirchofer et al. | |
| 6,312,412 B1 | 11/2001 | Saied et al. | |
| 6,319,233 B1 | 11/2001 | Jansen et al. | |
| 6,319,234 B1 | 11/2001 | Resfelli et al. | |
| 6,322,540 B1 | 11/2001 | Grabis | |
| 6,371,939 B2 | 4/2002 | Bergens et al. | |
| 6,387,074 B1 | 5/2002 | Horppu et al. | |
| 6,387,078 B1 | 5/2002 | Gillespie, III | |
| 6,413,237 B1 | 7/2002 | Caizza et al. | |
| 6,419,658 B1 | 7/2002 | Resfelli et al. | |
| D461,555 S | 8/2002 | Binet et al. | |
| 6,454,746 B1 * | 9/2002 | Bydlon et al. | 604/227 |
| 6,475,194 B2 | 11/2002 | Domici | |
| 6,509,015 B1 | 1/2003 | Salfeld et al. | |
| 6,517,517 B1 | 2/2003 | Farrugia et al. | |
| 6,544,234 B1 | 4/2003 | Gabriel | |
| 6,575,939 B1 | 6/2003 | Brunel | |
| 6,589,210 B1 | 7/2003 | Rolfe | |
| 6,656,163 B1 | 12/2003 | Marshall et al. | |
| 6,656,164 B1 | 12/2003 | Smith | |
| 6,673,035 B1 | 1/2004 | Rice et al. | |
| 6,692,469 B1 | 2/2004 | Weekes et al. | |
| 6,712,788 B2 | 3/2004 | Righi | |
| 6,743,203 B1 | 6/2004 | Pickhard | |
| 6,752,798 B2 | 6/2004 | McWethy | |
| 6,767,336 B1 | 7/2004 | Kaplan | |
| D494,270 S | 8/2004 | Reschke | |
| 6,773,415 B2 | 8/2004 | Heiniger | |
| 6,796,967 B2 | 9/2004 | Jensen | |
| 6,802,827 B2 | 10/2004 | Andersson | |
| 6,805,686 B1 | 10/2004 | Fathallah et al. | |
| 6,808,507 B2 | 10/2004 | Roser | |
| 6,817,989 B2 | 11/2004 | Svendsen | |
| 6,872,194 B2 | 3/2005 | Doyle et al. | |
| 6,926,697 B2 | 8/2005 | Malenchek | |
| 6,932,793 B1 | 8/2005 | Marshall et al. | |
| 6,945,960 B2 | 9/2005 | Barker | |
| 6,976,976 B2 | 12/2005 | Doyle | |
| 6,979,316 B1 * | 12/2005 | Rubin et al. | 604/156 |
| 6,986,760 B2 | 1/2006 | Giambattista | |
| 7,004,929 B2 | 2/2006 | McWethy | |
| D518,175 S | 3/2006 | Hardin et al. | |
| 7,056,306 B1 | 6/2006 | Halseth | |
| 7,223,394 B2 | 5/2007 | Salfeld et al. | |
| 7,320,682 B2 | 1/2008 | Cocker | |
| 7,361,160 B2 | 4/2008 | Hommann et al. | |
| 7,497,847 B2 | 3/2009 | Crawford | |
| 7,541,031 B2 | 6/2009 | Salfeld et al. | |
| 7,588,761 B2 | 9/2009 | Salfeld et al. | |
| 7,694,828 B2 | 4/2010 | Swift et al. | |
| 7,736,333 B2 | 6/2010 | Gillespie, III | |
| D622,374 S | 8/2010 | Julian et al. | |
| D629,509 S | 12/2010 | Julian et al. | |
| 7,863,426 B2 | 1/2011 | Wan et al. | |
| 7,919,264 B2 | 4/2011 | Maksymowych et al. | |
| D638,935 S * | 5/2011 | Gilmore et al. | D24/133 |
| 7,938,802 B2 | 5/2011 | Bicknell et al. | |
| 8,162,887 B2 | 4/2012 | Bicknell et al. | |
| 8,372,030 B2 * | 2/2013 | Dixon et al. | 604/68 |
| D677,380 S | 3/2013 | Julian et al. | |
| 2001/0005781 A1 | 6/2001 | Bergens | |
| 2001/0053894 A1 | 12/2001 | Steenfeldt-Jensen et al. | |
| 2002/0002344 A1 | 1/2002 | Douglas et al. | |
| 2002/0016563 A1 | 2/2002 | Hill et al. | |
| 2002/0042592 A1 | 4/2002 | Wilmot et al. | |
| 2002/0095120 A1 | 7/2002 | Larsen et al. | |
| 2002/0111587 A1 | 8/2002 | Hommann et al. | |
| 2002/0161337 A1 | 10/2002 | Shaw et al. | |
| 2002/0169408 A1 | 11/2002 | Beretta et al. | |
| 2002/0183690 A1 | 12/2002 | Arnisolle | |
| 2003/0004466 A1 | 1/2003 | Bitdinger et al. | |
| 2003/0004467 A1 | 1/2003 | Musick et al. | |
| 2003/0023203 A1 | 1/2003 | Lavi et al. | |
| 2003/0023205 A1 | 1/2003 | Botich et al. | |
| 2003/0050606 A1 | 3/2003 | Brand et al. | |
| 2003/0093036 A1 | 5/2003 | Crossman et al. | |
| 2003/0105430 A1 | 6/2003 | Lavi et al. | |
| 2003/0161744 A1 | 8/2003 | Vilks et al. | |
| 2003/0187401 A1 | 10/2003 | Doyle | |
| 2003/0212362 A1 | 11/2003 | Roser | |
| 2003/0229308 A1 | 12/2003 | Tsals et al. | |
| 2003/0236502 A1 | 12/2003 | De La Serna et al. | |
| 2004/0019326 A1 | 1/2004 | Gilbert et al. | |
| 2004/0024367 A1 | 2/2004 | Gilbert | |
| 2004/0025272 A1 * | 2/2004 | Stvartak et al. | 15/143.1 |
| 2004/0039336 A1 | 2/2004 | Amark et al. | |
| 2004/0039337 A1 | 2/2004 | Letzing | |
| 2004/0054319 A1 * | 3/2004 | Langley | A61M 5/20 604/67 |
| 2004/0054327 A1 | 3/2004 | Gillespie, III | |
| 2004/0147875 A1 | 7/2004 | Wallace et al. | |
| 2004/0154133 A1 * | 8/2004 | Polzin | B25F 5/006 16/430 |
| 2004/0199117 A1 | 10/2004 | Giambattista et al. | |
| 2004/0215151 A1 | 10/2004 | Marshall et al. | |
| 2004/0225262 A1 | 11/2004 | Fathallah et al. | |
| 2004/0249339 A1 * | 12/2004 | Willis | A61M 5/30 604/70 |
| 2005/0020979 A1 | 1/2005 | Westbye et al. | |
| 2005/0020984 A1 | 1/2005 | Lesch, Jr. | |
| 2005/0027255 A1 | 2/2005 | Lavi et al. | |
| 2005/0049550 A1 | 3/2005 | Kirchofer et al. | |
| 2005/0049561 A1 | 3/2005 | Hommann et al. | |
| 2005/0085776 A1 | 4/2005 | Hommann et al. | |
| 2005/0096597 A1 | 5/2005 | Crawford | |
| 2005/0101919 A1 | 5/2005 | Brunnberg | |
| 2005/0124940 A1 | 6/2005 | Martin et al. | |
| 2005/0137534 A1 | 6/2005 | Hommann | |
| 2005/0137571 A1 | 6/2005 | Hommann | |
| 2005/0165360 A1 | 7/2005 | Stamp | |
| 2005/0165361 A1 | 7/2005 | Marshall et al. | |
| 2005/0165362 A1 | 7/2005 | Slawson | |
| 2005/0165363 A1 | 7/2005 | Judson et al. | |
| 2005/0171476 A1 | 8/2005 | Judson et al. | |
| 2005/0171477 A1 | 8/2005 | Rubin et al. | |
| 2005/0209569 A1 | 9/2005 | Ishikawa et al. | |
| 2005/0222539 A1 | 10/2005 | Gonzales et al. | |
| 2005/0222540 A1 | 10/2005 | Kirchofer et al. | |
| 2005/0261634 A1 | 11/2005 | Karlsson | |
| 2005/0273054 A1 | 12/2005 | Asch | |
| 2005/0273055 A1 | 12/2005 | Harrisson et al. | |
| 2005/0273061 A1 | 12/2005 | Hommann et al. | |
| 2005/0277885 A1 | 12/2005 | Scherer | |
| 2005/0277886 A1 | 12/2005 | Hommann et al. | |
| 2005/0277893 A1 | 12/2005 | Liversidge | |
| 2005/0288633 A1 | 12/2005 | Jeffrey | |
| 2006/0030819 A1 | 2/2006 | Young et al. | |
| 2006/0036216 A1 | 2/2006 | Rimlinger et al. | |
| 2006/0037158 A1 * | 2/2006 | Foley | A46B 9/026 15/105 |
| 2006/0047250 A1 | 3/2006 | Hickinbotham et al. | |
| 2006/0069350 A1 | 3/2006 | Buenger et al. | |
| 2006/0069354 A1 | 3/2006 | Buenger et al. | |
| 2006/0100588 A1 | 5/2006 | Brunnberg et al. | |
| 2006/0111666 A1 | 5/2006 | Hommann et al. | |

(56) References Cited

U.S. PATENT DOCUMENTS

| | | | |
|---|---|---|---|
| 2006/0111674 A1 | 5/2006 | Vedrine | |
| 2006/0129089 A1* | 6/2006 | Stamp | 604/93.01 |
| 2006/0129122 A1 | 6/2006 | Wyrick | |
| 2006/0167413 A1 | 7/2006 | Marshall et al. | |
| 2006/0189933 A1 | 8/2006 | Alheidt | |
| 2006/0253083 A1 | 11/2006 | Liu | |
| 2007/0049865 A1 | 3/2007 | Radmer et al. | |
| 2007/0129674 A1 | 6/2007 | Liversidge | |
| 2007/0142776 A9 | 6/2007 | Kovelman et al. | |
| 2007/0161960 A1 | 7/2007 | Chen et al. | |
| 2007/0197976 A1* | 8/2007 | Jacobs et al. | 604/218 |
| 2007/0239117 A1 | 10/2007 | Chelak | |
| 2008/0097337 A1 | 4/2008 | Judd | |
| 2008/0120798 A1* | 5/2008 | Sorrentino et al. | 15/106 |
| 2008/0195052 A1* | 8/2008 | Hjertman | A61M 5/3129 604/187 |
| 2008/0195056 A1* | 8/2008 | Bishop et al. | 604/218 |
| 2008/0208125 A1 | 8/2008 | Bicknell et al. | |
| 2008/0208140 A1 | 8/2008 | Barrelle | |
| 2008/0269692 A1 | 10/2008 | James | |
| 2008/0300549 A1 | 12/2008 | Verespej | |
| 2009/0024076 A1 | 1/2009 | Babaev | |
| 2009/0024093 A1 | 1/2009 | Carrel | |
| 2009/0036870 A1 | 2/2009 | Mounce et al. | |
| 2009/0157012 A1* | 6/2009 | Magne | A61M 5/3243 604/198 |
| 2009/0240195 A1* | 9/2009 | Schrul et al. | 604/71 |
| 2009/0240210 A1 | 9/2009 | Walton | |
| 2009/0299328 A1 | 12/2009 | Mudd et al. | |
| 2010/0080087 A1* | 4/2010 | Shupp | 368/14 |
| 2010/0160869 A1 | 6/2010 | Liversidge | |
| 2010/0160894 A1 | 6/2010 | Julian et al. | |
| 2011/0054414 A1 | 3/2011 | Shang et al. | |
| 2011/0146015 A1* | 6/2011 | Moskovich | A46B 5/02 15/167.1 |
| 2011/0178469 A1* | 7/2011 | Johnston | A61M 5/2033 604/187 |
| 2011/0178500 A1 | 7/2011 | Shang et al. | |
| 2011/0218502 A1* | 9/2011 | Iio et al. | 604/264 |
| 2011/0257602 A1* | 10/2011 | Watanabe | A61M 5/20 604/189 |
| 2012/0022499 A1 | 1/2012 | Anderson et al. | |
| 2012/0107783 A1 | 5/2012 | Julian et al. | |
| 2012/0197209 A1 | 8/2012 | Bicknell et al. | |
| 2012/0233834 A1 | 9/2012 | Szechinski et al. | |
| 2012/0238961 A1 | 9/2012 | Julian et al. | |
| 2012/0255136 A1* | 10/2012 | Jimenez | A46B 5/02 15/167.1 |

FOREIGN PATENT DOCUMENTS

| | | |
|---|---|---|
| DE | 60207576 | 6/2006 |
| EP | 0068864 | 1/1983 |
| EP | 1334740 | 8/2003 |
| EP | 1364667 | 11/2003 |
| EP | 1523360 | 4/2005 |
| EP | 2067496 | 6/2009 |
| EP | 2085104 | 8/2009 |
| GB | 2243552 | 11/1991 |
| GB | 2388033 | 11/2003 |
| GB | 2424837 A | 10/2006 |
| JP | 50-14835 | 5/1975 |
| JP | 5-161712 | 6/1993 |
| JP | 2001-512038 | 8/2001 |
| JP | 2006507060 | 3/2006 |
| RU | 2004256 | 12/1993 |
| RU | 2131748 | 6/1999 |
| RU | 2169584 | 6/2001 |
| WO | WO 93/13819 A1 | 7/1993 |
| WO | WO 94/09839 A1 | 5/1994 |
| WO | WO 94/13342 A1 | 6/1994 |
| WO | WO 94/26333 A1 | 11/1994 |
| WO | 98/55168 A1 | 12/1998 |
| WO | WO 99/22789 A1 | 5/1999 |
| WO | WO 99/22792 A1 | 5/1999 |
| WO | 99/40958 A1 | 8/1999 |
| WO | WO 01/37908 A1 | 5/2001 |
| WO | WO 01/62319 A2 | 8/2001 |
| WO | WO 03/039633 A2 | 5/2003 |
| WO | WO 03/077968 A2 | 9/2003 |
| WO | WO 03/097133 A1 | 11/2003 |
| WO | WO 03/099358 | 12/2003 |
| WO | WO 04/000397 | 12/2003 |
| WO | WO 2004/047892 | 6/2004 |
| WO | WO 2004/060451 A1 | 7/2004 |
| WO | WO 2004/067068 A1 | 8/2004 |
| WO | WO 2005/002653 | 1/2005 |
| WO | WO 2005/046765 A2 | 5/2005 |
| WO | WO 2005/079889 A1 | 9/2005 |
| WO | WO 2005/090836 | 9/2005 |
| WO | 2005/097238 A2 | 10/2005 |
| WO | WO 2005/0113039 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115511 A1 | 12/2005 |
| WO | WO 2005/115512 A1 | 12/2005 |
| WO | WO 2005/115513 A1 | 12/2005 |
| WO | WO 2005/115516 A1 | 12/2005 |
| WO | WO 2006/000785 | 1/2006 |
| WO | WO 2006/058061 A1 | 6/2006 |
| WO | WO 2008/005315 | 1/2008 |
| WO | 2010055608 A1 | 5/2010 |

OTHER PUBLICATIONS

Communication of a Notice of Opposition issued in European Application No. 04822031.3-1526, dated Jan. 6, 2010.

Communication pursuant to Article 96(2) EPC issued in European Application No. 04822031.3-1526, dated May 31, 2007.

Communication under Rule 112 EPC issued in European Application No. 04822031.3, dated Mar. 13, 2007.

International Search Report issued in International Application No. PCT/GB2005/002487, dated Aug. 19, 2005.

Written Opinion issued in International Application No. PCT/GB2005/002487, dated Dec. 23, 2006.

International Preliminary Report on Patentability issued in International Application No. PCT/GB2005/002487, dated Sep. 7, 2006.

International Search Report issued in International Application No. PCT/US2011/033504, dated Jul. 8, 2011.

Written Opinion issued in International Application No. PCT/US2011/033504, dated Jul. 8, 2011.

International Search Report issued in International Application No. PCT/US2007/015095, dated Sep. 11, 2008.

Written Opinion issued in International Application No. PCT/US2007/015095, dated Sep. 11, 2008.

International Preliminary Report on Patentability issued in International Application No. PCT/US2007/015095, dated Jun. 19, 2009.

International Search Report issued in International Application No. PCT/US2010/033012, dated Jul. 2, 2010.

Written Opinion issued in International Application No. PCT/US2010/033012, dated Jul. 2, 2010.

International Search Report issued in International Application No. PCT/US2010/060496, dated Feb. 16, 2011.

Written Opinion issued in International Application No. PCT/US2010/060496, dated Feb. 16, 2011.

International Search Report issued in International Application No. PCT/US2004/013278, dated May 30, 2005.

Written Opinion issued in International Application No. PCT/US2004/013278, dated Oct. 29, 2006.

International Preliminary Report on Patentability issued in International Application No. PCT/US2004/013278, dated Nov. 1, 2006.

Office Action issued in Russian Application No. 2006145501/14(049694), dated May 21, 2009.

Decision on Grant issued in Russian Application No. 2006145501/14(049694), dated Nov. 2, 2009.

Decision on Grant issued in Russian Application No. 2009102986/14(003862), dated Jun. 30, 2011.

(56) References Cited

OTHER PUBLICATIONS

Notice of Reasons for Rejection issued in Japanese Application No. 2007-517459, dated Aug. 24, 2010.
Notice of Reasons for Rejection issued in Japanese Application No. 2007-517459, dated Mar. 8, 2011.
Office Action issued in Mexican Application No. PA/a/2006/015056, dated Jul. 28, 2010.
Office Action issued in Mexican Application No. PA/a/2006/015056, dated Apr. 1, 2011.
Reexamination Decision issued in Chinese Application No. 200580020958.6, dated Jun. 13, 2011.
Notification of Reexamination issued in Chinese Application No. 200580020958.6, dated Aug. 17, 2010.
Rejection Decision issued in Chinese Application No. 200580020958.6, dated Jun. 5, 2009.
Office Action issued in Chinese Application No. 200580020958.6, dated Sep. 5, 2008.
Office Action issued in Australian Application No. 2005256832, dated Apr. 18, 2011.
Office Action issued in Australian Application No. 2005256832, dated Feb. 22, 2010.
Examination Report issued in New Zealand Application No. 552340, dated Apr. 27, 2009.
Examination Report issued in New Zealand Application No. 552340, dated Aug. 12, 2010.
Notification of Provisional Rejection issued in Korean Application No. 10-2006-7026814, dated Jul. 19, 2011.
BD Preventis, Shielding System for Prefilled Syringes, http://www.bd.com/pharmaceuticals/products/safety-engineered.asp, last accessed Aug. 26, 2010.
"Abbott Receives FDA Approval for New Humira Delivery Device," Press Release, dated Jun. 26, 2006 (color).
Correspondence from Dept. of Health & Human Services, Food and Drug Administration, to Robert Shaw/Owen Mumford, Inc. regarding Section 501(k) notification to market device, dated Nov. 10, 1999.
Correspondence from Dept. of Health & Human Services, Food and Drug Administration, to Robert Shaw/Owen Mumford, Inc. regarding Section 501(k) notification to market device, dated Mar. 6, 2000.
Owen Mumford drawing/schematic of the Abbott-Plunger AUTOject Mini, dated Mar. 25, 2002, Drawing No. P02 207.
Owen Mumford drawing/schematic of the Plunger-Miniject dated Mar. 30, 1993, Drawing No. P93.022.
Owen Mumford drawing/schematic of the Plunger-Miniject dated Mar. 30, 1993, Drawing No. AJ 358.
Owen Mumford drawing/schematic A of the Plunger-Miniject dated Sep. 5, 1997, Drawing No. AJ 654.
Owen Mumford drawing/schematic B of the Plunger-Miniject dated Sep. 5, 1997, Drawing No. AJ 654.
Office Action issued in Canadian Application No. 2,571,571, dated Oct. 24, 2011.
Office Action issued in Chinese Application No. 201010576413.6, dated Nov. 2, 2011.
International Preliminary Report on Patentability issued in International Application No. PCT/US2010/033012, dated Nov. 1, 2011.
Decision of Final Rejection issued in Japanese Application No. 2007-517459, dated Jan. 10, 2012.
Summons to Attend Oral Proceedings pursuant to Rule 115(1) EPC, dated Apr. 20, 2012.
Notice of Rejection issued in Japanese Application No. 2009-518284, dated May 29, 2012.
International Search Report issued in International Application No. PCT/US2012/022433, dated Jul. 5, 2012.
Written Opinion issued in International Application No. PCT/US2012/022433, dated Jul. 5, 2012.
Written Opinion of the Austrian Patent Office for Singapore Patent Application No. 201305645-2 dated Jul. 23, 2014.
English Translation of the Office Action by the Colombian Patent Office for Colombian Patent No. 13198257 dated Nov. 21, 2014.
English Translation of the First Office Action by the State Intellectual Property Office of PRC for Chinese Application No. 201280014851.0 dated Nov. 19, 2014.
International Preliminary Report on Patentability on International Application No. PCT/US2012/022433 issued Jul. 30, 2013.
Patent Examination Report by IP Australia, issued on May 30, 2014.
First Examination Report by New Zealand Intellectual Property Office issued May 26, 2014.
European Search Report on Application No. 1416292.2, issued on May 23, 2014.
European Examination Report in Application No. 12701430.6, issued on Apr. 8, 2014.
Office Action issued by the Dominican Patent Office for application 2013-0167 on May 7, 2015.
Translation of the First Office Action issued by the Mexican Institute of Industrial Property (IMPI) for application No. MX/a/2013/008611 on Jul. 3, 2015.
Communication pursuant to Article 94(3) EPC by European Patent Office for European application No. 12701430.6 dated Aug. 21, 2015.

* cited by examiner

AUTOMATIC INJECTION DEVICES HAVING OVERMOLDED GRIPPING SURFACES

RELATED APPLICATIONS

This application is a non-provisional of and claims priority to U.S. Provisional Patent Application No. 61/435,465, filed Jan. 24, 2011, the entire contents of which are expressly incorporated herein by reference in their entirety.

BACKGROUND

Automatic injection devices offer an alternative to manually-operated syringes for administering therapeutic agents into patients' bodies and allowing patients to self-administer therapeutic agents. Automatic injection devices may be used to administer medications under emergency conditions, for example, to administer epinephrine to counteract the effects of a severe allergic reaction. Automatic injection devices have also been described for use in administering anti-arrhythmic medications and selective thrombolytic agents during a heart attack. See, for example, U.S. Pat. Nos. 3,910,260; 4,004, 577; 4,689,042; 4,755,169; and 4,795,433, the entire contents of which are incorporated herein in their entirety by reference. Various types of automatic injection devices are also described in, for example, U.S. Pat. Nos. 3,941,130; 4,261, 358; 5,085,642; 5,092,843; 5,102,393; 5,267,963; 6,149,626; 6,270,479; and 6,371,939; and International Patent Publication No. WO/2008/005315, the entire contents of which are incorporated herein in their entirety by reference.

Conventionally, an automatic injection device houses a syringe and, when operated, causes the syringe to move forwardly and a needle to project from the housing so that a therapeutic agent contained in the syringe is ejected into a patient's body.

SUMMARY

Exemplary embodiments provide automatic injection devices, housing components for automatic injection devices and methods for fabricating the same. An exemplary housing of an automatic injection device may be overmolded with one or more gripping surfaces to facilitate gripping and manipulation of the automatic injection device by a user when performing an injection. In an exemplary embodiment, an overmolded left gripping surface may extend along a left side of the housing and an overmolded right gripping surface may extend along a right side of the housing opposite to the left side.

In accordance with an exemplary embodiment, an automatic injection device is provided with a housing enclosing a cavity for accommodating a container. A first overmolded gripping surface is provided to extend longitudinally along a portion of the housing on a first exterior surface of the housing. A second overmolded griping surface is provided to extend longitudinally along a portion of the housing on a second exterior surface of the housing opposite to the first exterior surface.

In an exemplary embodiment, the first and second overmolded gripping surfaces on the housing are formed of a first material having a first touch perception, and non-gripping surfaces on the housing are formed of a second material having a second touch perception. In an exemplary embodiment, the first and second overmolded gripping surfaces on the housing are formed of a first material having a first hardness, and non-gripping surfaces on the housing are formed of a second material having a second higher hardness.

In an exemplary embodiment, the automatic injection device includes a removable distal cap for protectively covering an injection needle couplable to the container, an exterior surface of the distal cap including an overmolded gripping surface for facilitating gripping and removal of the distal cap. In an exemplary embodiment, the automatic injection device includes a firing button protruding from an aperture in the housing and including an overmolded contact surface for facilitating actuation of the firing button by a user. In an exemplary embodiment, the automatic injection device includes a proximal terminal end for covering a proximal end of the automatic injection device, the proximal terminal end having an overmolded exterior surface. In an exemplary embodiment, a top surface of the proximal terminal end includes a recessed surface for directing and facilitating accommodation of a user's hand or finger for gripping the automatic injection device.

In accordance with another exemplary embodiment, a method is provided for assembling an automatic injection device. The method includes providing a housing enclosing a cavity for accommodating a container. The method includes overmolding, on the housing, a first gripping surface extending longitudinally along a portion of the housing on a first exterior surface of the housing. The method also includes overmolding, on the housing, a second gripping surface extending longitudinally along a portion of the housing on a second exterior surface of the housing opposite to the first exterior surface.

In an exemplary embodiment, the first and second gripping surfaces on the housing are formed of a first material having a first touch perception, and non-gripping surfaces on the housing are formed of a second material having a second touch perception. In an exemplary embodiment, the first and second gripping surfaces on the housing are formed of a first material having a first hardness, and non-gripping surfaces on the housing are formed of a second material having a second higher hardness.

In an exemplary embodiment, the method includes overmolding a gripping surface on an exterior surface of a distal cap to facilitate gripping and removal of the distal cap, and coupling the distal cap to a distal end of the housing for protectively covering an injection needle. In an exemplary embodiment, the method includes overmolding a gripping surface on a firing button to facilitate activation of the firing button, and providing the firing button within the cavity so that part of the firing button protrudes from an aperture in the housing.

In an exemplary embodiment, the method includes overmolding a gripping surface on an exterior surface of a proximal terminal end, and coupling the proximal terminal end to a proximal end of the housing. In an exemplary embodiment, a top surface of the proximal terminal end includes a recessed surface for directing a user's hand or finger for gripping the automatic injection device.

In accordance with another exemplary embodiment, an automatic injection device is provided including a housing enclosing a cavity for accommodating a container. The housing includes a first overmolded gripping region, a second overmolded gripping region, and a recessed region abutting the first and second overmolded gripping regions.

In an exemplary embodiment, the recessed region is disposed between the first and second overmolded gripping regions. In an exemplary embodiment, a width of the housing at the recessed region is smaller than a width of the housing at the first overmolded gripping region and a width of the housing at the second overmolded gripping region. In an exemplary embodiment, the recessed region lacks a gripping surface.

In an exemplary embodiment, the first overmolded gripping region is formed by a proximal terminal end of the housing having an exterior surface that is overmolded with a gripping surface. In an exemplary embodiment, the second overmolded gripping region of the housing has a tapered tubular structure.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which.

DETAILED DESCRIPTION

Figure 1:
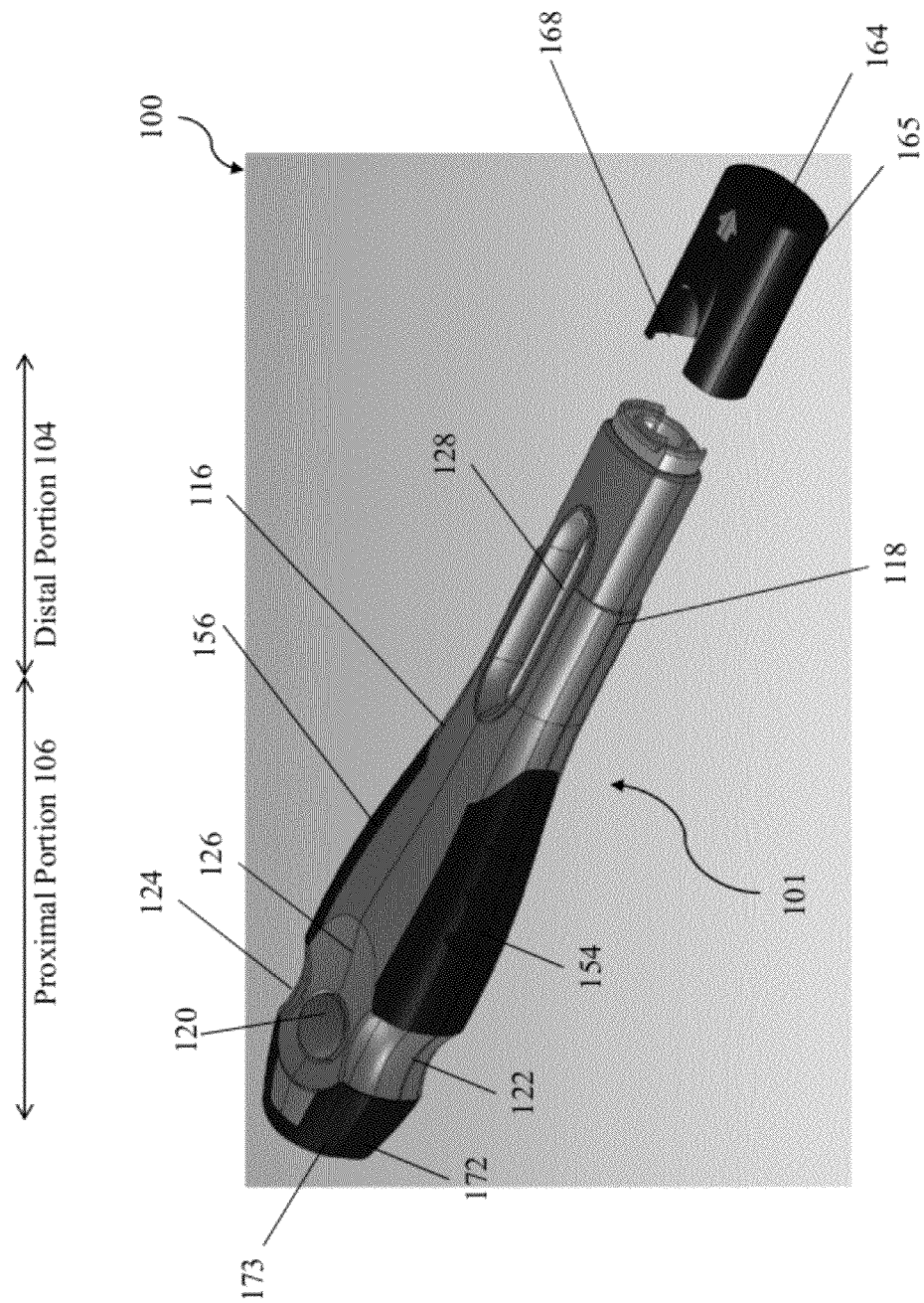
FIG. 1 is a left side perspective view illustrating an exemplary automatic injection device in which a removable distal cap is removed and pictured separately from the housing of the device.

Exemplary embodiments provide automatic injection devices having housings that are particularly designed and configured for reliable, safe, ergonomic and comfortable handling by users. Exemplary embodiments also provide housing components for automatic injection devices that are particularly designed and configured for reliable, safe, ergonomic and comfortable handling by users. Exemplary embodiments also provide methods for fabricating exemplary housings for automatic injection devices and automatic injection devices including exemplary housings.

In one exemplary embodiment, one or more overmolded gripping surfaces may be provided on an exterior surface of an exemplary automatic injection device housing in order to allow the device to be easily, comfortably and reliably gripped and manipulated by a user. The exemplary overmolded gripping surfaces are particularly configured and positioned on the housing to prevent slippage from the hands of the user, and thereby to avoid injury to the user and others in the vicinity. Furthermore, the exemplary overmolded gripping surfaces are particularly configured and positioned to be ergonomic and comfortable to use, particularly by physically weak users, for example, older users, users who suffer from rheumatoid arthritis, and the like.

In user tests performed using exemplary automatic injection devices, test participants appreciated exemplary overmolded gripping surfaces on the sides of the devices and the relatively large size and ergonomic shape of the device. The test participants provided high ratings for handling and grip of exemplary devices, in which the overmolded gripping surfaces were the primary factor in test participants' high ratings of exemplary device configurations for handling and grip, compared to devices without overmolded gripping surfaces. For several usability factors, there was a significant positive correlation between Cochin scores and exemplary device configurations, which indicates that exemplary devices are well-suited for use by users with hand dysfunction.

An exemplary automatic injections device may contain and may be used to administer a dose of a TNF$\alpha$ inhibitor. In an exemplary embodiment, the TNF$\alpha$ inhibitor may be a human TNF$\alpha$ antibody or antigen-biding portion thereof. In an exemplary embodiment, the human TNF$\alpha$ antibody or antigen-binding portion thereof may be adalimumab (HUMIRA®) or golimumab.

I. DEFINITIONS

Certain terms are defined in this section to facilitate understanding of exemplary embodiments.

The terms "automatic injection device" and "autoinjector," as used herein, refer to a device that enables a patient to self-administer a therapeutically effective dose of a therapeutic agent, wherein the device differs from a conventional syringe by the inclusion of a mechanism for automatically delivering the therapeutic agent to the patient by injection when the mechanism is engaged.

The terms "vessel" and "container," as used herein, refer to a syringe or cartridge that may be used in an exemplary automatic injection device for holding a dose of a therapeutic agent.

The terms "syringe" and "cartridge," as used herein, refer to a sterile barrel portion of an automatic injection device that is filled with a dose of a therapeutic agent prior to distribution or sale of the device to a patient or other non-medical professional for administration of the therapeutic agent to a patient. In an exemplary embodiment, a distal end of the barrel portion of a syringe may be coupled to a sterile hypodermic injection needle. In an exemplary embodiment, a distal end of the barrel portion of a cartridge may not be coupled to an injection needle. That is, in exemplary embodiments, a syringe may be a cartridge with a pre-attached injection needle coupled to its barrel portion.

Exemplary embodiments described herein with reference to a syringe assembly may also be implemented using a cartridge assembly. Similarly, exemplary embodiments described herein with reference to a cartridge assembly may also be implemented using a syringe assembly.

The term "pre-filled syringe," as used herein, refers to a syringe that is filled with a therapeutic agent immediately prior to administration of the therapeutic agent to a patient, and a syringe that is filled with a therapeutic agent and stored in this pre-filled form for a period of time before administration of the therapeutic agent to a patient.

The terms "injection needle" and "needle," as used herein, refer to a needle in an automatic injection device that is inserted into a patient's body to deliver a dose of a therapeutic agent into the patient's body. In an exemplary embodiment, the injection needle may be directly coupled to or may otherwise be in contact with a syringe assembly or a cartridge assembly that holds a dose of the therapeutic agent. In another exemplary embodiment, the injection needle may be indirectly coupled to the syringe or cartridge assembly, for example, via a syringe needle and/or a transfer mechanism that provides fluid communication between the syringe or cartridge assembly and the injection needle.

The term "pre-injection state," as used herein, refers to a state of an automatic injection device prior to activation of the device, i.e., prior to the start of delivery of a therapeutic agent contained in the device.

The term "injection state," as used herein, refers to one or more states of an automatic injection device during the delivery of a therapeutic agent contained in the device.

The term "post-injection state," as used herein, refers to completion of delivery of a therapeutically effective dose of a therapeutic agent contained in the device, or removal of the device from the patient prior to completion of delivery of a therapeutically effective dose of the therapeutic agent.

An automatic injection device provided in accordance with exemplary embodiments may include a "therapeutically effective amount" or a "prophylactically effective amount" of an antibody or antibody portion of the invention. A "therapeutically effective amount," as used herein, refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the patient, and the ability of the antibody, antibody portion, or other TNFα inhibitor to elicit a desired response in the patient. A therapeutically effective amount is also one in which any toxic or detrimental effects of the antibody, antibody portion, or other TNFα inhibitor are outweighed by the therapeutically beneficial effects. A "prophylactically effective amount," as used herein, refers to an amount effective, at dosages and for periods of time necessary, to achieve the desired prophylactic result. Typically, since a prophylactic dose is used in patients prior to or at an earlier stage of disease, the prophylactically effective amount will be less than the therapeutically effective amount.

The terms "substance" and "therapeutic agent," as used herein, refer to any type of drug, biologically active agent, biological substance, chemical substance or biochemical substance that is capable of being administered in a therapeutically effective amount to a patient employing exemplary automatic injection devices. Exemplary therapeutic agents usable in exemplary automatic injection devices may include, but are not limited to, agents in a liquid state. Such agents may include, but are not limited to, adalimumab (HUMIRA®) and proteins that are in a liquid solution, e.g., fusion proteins and enzymes. Examples of proteins in solution include, but are not limited to, Pulmozyme (Dornase alfa), Regranex (Becaplermin), Activase (Alteplase), Aldurazyme (Laronidase), Amevive (Alefacept), Aranesp (Darbepoetin alfa), Becaplermin Concentrate, Betaseron (Interferon beta-1b), BOTOX (Botulinum Toxin Type A), Elitek (Rasburicase), Elspar (Asparaginase), Epogen (Epoetin alfa), Enbrel (Etanercept), Fabrazyme (Agalsidase beta), Infergen (Interferon alfacon-1), Intron A (Interferon alfa-2a), Kineret (Anakinra), MYOBLOC (Botulinum Toxin Type B), Neulasta (Pegfilgrastim), Neumega (Oprelvekin), Neupogen (Filgrastim), Ontak (Denileukin diftitox), PEGASYS (Peginterferon alfa-2a), Proleukin (Aldesleukin), Pulmozyme (Dornase alfa), Rebif (Interferon beta-1a), Regranex (Becaplermin), Retavase (Reteplase), Roferon-A (Interferon alfa-2), TNKase (Tenecteplase), and Xigris (Drotrecogin alfa), Arcalyst (Rilonacept), NPlate (Romiplostim), Mircera (methoxypolyethylene glycol-epoetin beta), Cinryze (C1 esterase inhibitor), Elaprase (idursulfase), Myozyme (alglucosidase alfa), Orencia (abatacept), Naglazyme (galsulfase), Kepivance (palifermin) and Actimmune (interferon gamma-1b).

The term "dose" or "dosage," as used herein, refers to an amount of a therapeutic agent, such as a TNFα inhibitor, which is administered to a patient preferably using the wearable automatic injection device of the invention. In one embodiment, the dose comprises an effective amount, for example, including, but not limited to, 20 mg, 30 mg, 40 mg, 50 mg, 60 mg, 70 mg, 80 mg, 90 mg, 100 mg, 110 mg, 120 mg, 130 mg, 140 mg, 150 mg, and 160 mg, of the TNFα inhibitor adalimumab.

The term "dosing," as used herein, refers to the administration of a therapeutic agent (e.g., an anti-TNFα antibody) to achieve a therapeutic objective (e.g., treatment of rheumatoid arthritis).

The term "dosing regimen," as used herein, refers to a treatment schedule for a therapeutic agent, such as a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The term "treatment," as used herein, refers to therapeutic treatment, as well as prophylactic or suppressive measures, for the treatment of a disorder, such as a disorder in which TNFα is detrimental, e.g., rheumatoid arthritis.

The term "patient" or "user," as used herein, refers to any type of animal, human or non-human, that may be administered a therapeutic agent using exemplary automatic injection devices.

The term "proximal" refers to a portion or end or component of an exemplary automatic injection device that is farthest from an injection site on a patient's body when the device is held against the patient for an injection or for mimicking an injection.

The term "distal" refers to a portion or end or component of an exemplary automatic injection device that is closest to an injection site on a patient's body when the device is held against the patient for an injection or for mimicking an injection.

The term "planar" is used herein, in a broad lay sense, to mean exactly planar or approximately planar within some tolerance from the exactly planar.

The term "concave" is used herein, in a broad lay sense, to mean exactly concave or approximately concave within some tolerance from the exactly concave.

The term "convex" is used herein, in a broad lay sense, to mean exactly convex or approximately convex within some tolerance from the exactly convex.

The term "elliptical" is used herein, in a broad lay sense, to mean exactly elliptical or approximately elliptical within some tolerance from the exactly elliptical.

The term "oval" is used herein, in a broad lay sense, to mean exactly oval or approximately oval within some tolerance from the exactly oval.

The term "rectangular" is used herein, in a broad lay sense, to mean exactly rectangular or approximately rectangular within some tolerance from the exactly rectangular.

The term "parallel" is used herein, in a broad lay sense, to mean exactly parallel or approximately parallel within some tolerance from the exactly parallel.

The term "straight" is used herein, in a broad lay sense, to mean exactly straight or approximately straight within some tolerance from the exactly straight.

The term "equal" is used herein, in a broad lay sense, to mean exactly equal or approximately equal within some tolerance.

The term "adjacent" is used herein, in a broad lay sense, to mean immediately adjacent or approximately adjacent within some tolerance.

The term "abut" is used herein, in a broad lay sense, to mean immediately abutting or approximately abutting within some tolerance.

The term "transverse axis" is used herein to refer to an axis that is substantially perpendicular to a longitudinal axis.

II. EXEMPLARY EMBODIMENTS

Exemplary embodiments are described below with reference to certain illustrative embodiments. While exemplary embodiments are described with respect to using an automatic injection device to provide an injection of a dose of a therapeutic agent, one of ordinary skill in the art will recognize that exemplary embodiments are not limited to the illustrative embodiments and that exemplary automatic injection devices may be used to inject any suitable therapeutic agent into a patient. In addition, components of exemplary automatic injection devices and methods of making and using exemplary automatic injection devices are not limited to the illustrative embodiments described below.

FIGS. 1-8 illustrate an exemplary automatic injection device 100 having one or more overmolded gripping surfaces for facilitating gripping and manipulation of the device. The figures indicate a longitudinal axis L that runs substantially along the length of the device 100, a first transverse axis H that runs substantially perpendicular to the longitudinal axis L of the device, and a second transverse axis V that runs substantially perpendicular to both longitudinal axis L and first transverse axis H.

In some exemplary embodiments, an exemplary length of the device 100 may be about 4, 4.5, 4.8, 5, 5.5, 6, 6.5, 6.6, 6.7, 6.8, 6.9, 7, 7.5, 8, 8.5, 9, 9.5, 10 inches, but is not limited to these exemplary lengths. In some exemplary embodiments, an exemplary width of the device 100 (at its widest location) may be about 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0 inches, but is not limited to these exemplary widths. In some exemplary embodiments, an exemplary thickness of the device 100 (at its thickest location) may be about 0.1, 0.2, 0.3, 0.4, 0.5, 0.6, 0.7, 0.8, 0.9, 1.0, 1.1, 1.11, 1.12, 1.13, 1.14, 1.15, 1.16, 1.17, 1.18, 1.19, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0 inches, but is not limited to these exemplary thicknesses. In an exemplary embodiment, the device 100 may have an exemplary length of about 6.69 inches, an exemplary width of about 1.46 inches at the widest portion, and an exemplary thickness of about 1.15 inches at the thickest portion. In another exemplary embodiment, the device 100 may have an exemplary length of about 4.8 inches, an exemplary width of about 0.8 inches at the widest portion, and an exemplary thickness of about 0.6 inches at the thickest portion. The exemplary dimensions of the recited exemplary devices allow the device to be conformably and ergonomically held in the grip of a user's hand. This allows a user to reliably and comfortably grip and manipulate the device in order to perform an injection.

Exemplary automatic injection device 100 may include an outer housing 101 for housing a container, such as a syringe or cartridge. The container may be pre-filled with a dose of a therapeutic agent to be injected into a patient's body. The housing 101 of the device, in its assembled form, may have any suitable size and shape for storing and dispensing the dose of the therapeutic agent. The assembled housing 101 may have a shape that is designed and configured to be conformable to a user's hand and so that the user can comfortably and reliably hold the device 100 during an injection. In an exemplary embodiment, the assembled housing 101 may have an elongated structure so that its length taken along the longitudinal axis L is much greater than its width taken along the first transverse axis H and its thickness taken along a second transverse axis V. An exemplary ratio of the length to the width (at the widest location) of the device may be, but is not limited to, 2:1, 3:1, 4:1, 5:1, 6:1, 7:1, 8:1, 9:1, 10:1, all intermediate ratios, and the like. An exemplary ratio of the length to the thickness (at the thickest location) of the device may be, but is not limited to, 2:1, 3:1, 4:1, 5:1, 6:1, 7:1, 8:1, 9:1, 10:1, all intermediate ratios, and the like.

Figure 2:
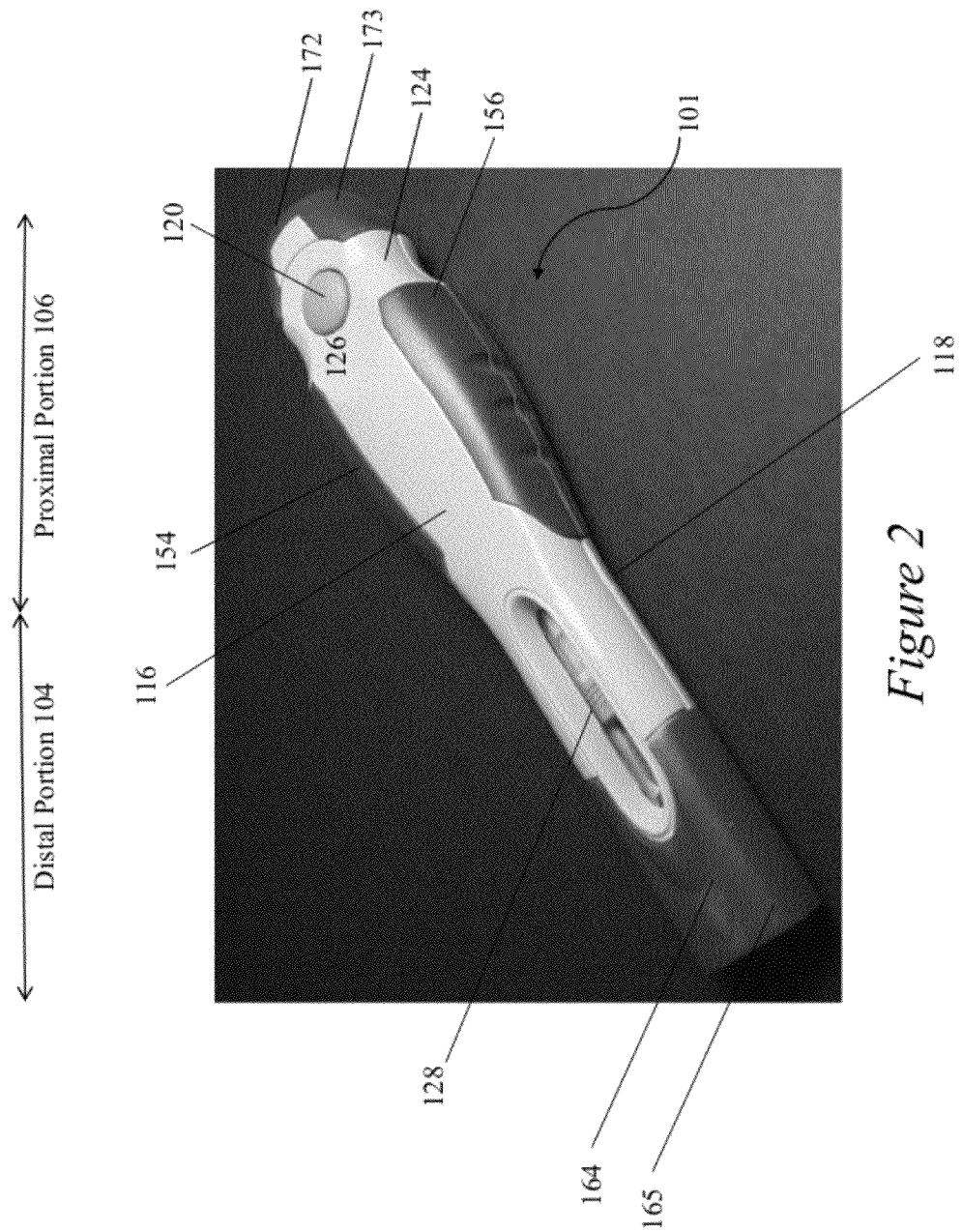
FIG. 2 is a right side perspective view illustrating the exemplary automatic injection device of FIG. 1.

FIG. 1 is a left side perspective view illustrating an exemplary automatic injection device 100 having an outer housing 101. FIG. 2 is a right side perspective view of the exemplary automatic injection device 100 of FIG. 1. In an exemplary embodiment, the housing 101 of the device 100 may have a tapered tubular structure with a substantially elliptical or oval cross-section. In the tapered tubular structure, the width of the housing 101 may be larger at a proximal portion 106 of the housing 101 than at a distal portion 104 of the housing 101. The tapered tubular shape of the exemplary housing allows the device to be streamlined and to be conformably and ergonomically held in and manipulated by a user's hand.

The housing 101 of the device 100 may be formed of a plurality of body components that are assembled together. In an exemplary embodiment, the housing 101 may be formed from a first body portion 116 and a second body portion 118 that, when cooperatively engaged to each other along their peripheral edges, enclose and provide a cavity therebetween. The first and second body portions may be cooperatively engaged to each other using any suitable technique including, but not limited to, bonding, gluing, ultrasonic welding, friction fit, snap fit, interference fit, screws, attachment between corresponding protrusions and recesses, and the like. One of ordinary skill in the art will recognize that, in other exemplary embodiments, the cavity of the device may be enclosed in a single body component or in three or more body components when assembled together.

A firing button 120 may extend from a surface of the first body portion 116. The firing button 120, when activated by a user, may cause an injection to be performed by the device 100. In an exemplary embodiment, a recessed or concave portion 126 may be provided on the first body portion 116 abutting the firing button 120 to facilitate activation of the firing button 120. The recessed portion 126 may surround the firing button 120 in an exemplary embodiment to accommodate a user's finger as the user presses on the firing button 120.

A transparent inspection window 128 may be provided in a surface of the first body portion 116 to allow a user to view the contents of the device 100. The transparent inspection window 128 may allow the user to view a therapeutic agent contained in the device 100, for example, to ensure clarity of the agent, and to view an end-of-injection indicator that materializes at the end of a successful injection. An exemplary inspection window 128 may be substantially elongated in shape, for example, an elongated rectangle (with sharp or rounded edges), an elongated elliptical shape, and the like, although other shapes are possible. In the elongated inspection window 128, the length extending along the longitudinal axis L may be substantially greater than the width extending along the first transverse axis H. In exemplary embodiments, a ratio between the length and the width of the inspection window may include, but is not limited to, 1.5:1, 2.0:1, 2.5:1, 3.0:1, 3.5:1, 4.0:1, 4.5:1, 5:1, all intermediate ratios, and the like.

A proximal terminal end 172 of the device housing may be provided to cover the proximal end of the device 100. In an exemplary embodiment, the proximal terminal end 172 may be coupled to the proximal end of the assembled first and second body portions. The proximal terminal end 172 may take any suitable size and shape. In an exemplary embodiment, the proximal terminal end 172 may have a substantially tubular configuration with a substantially oval or elliptical shape. In an exemplary embodiment, at least part of the exterior surface of the proximal terminal end 172 may be overmolded with one or more gripping surfaces 173 to facilitate gripping of the proximal portion of the device. In an exemplary embodiment, the entire exterior surface of the proximal terminal end 172 may be covered by an overmolded gripping surface 173. Corresponding recesses may be provided on the exterior surface of the proximal terminal end 172 to accommodate the gripping surfaces.

A removable distal cap 164 may be coupled to the distal end of the assembled first and second body portions to cover the distal end of the device 100 in order to prevent exposure of the injection needle prior to an injection. The distal cap 164 protects against accidental and/or unwanted contact of a user with the injection needle. The distal cap 164 also protects against damage to and contamination of the injection needle when the device is not in use. The distal cap 164 may take any suitable size and shape. In an exemplary embodiment, the distal cap 164 may have a substantially tubular configuration with a substantially oval or elliptical shape. In an exemplary embodiment, a front surface of the distal cap 164 may have a concave cutout portion 168 for accommodating part of the inspection window 128.

In an exemplary embodiment, the exterior surface of the distal cap 164 may lack overmolded gripping surfaces. In other exemplary embodiments, the exterior surface of the distal cap 164 may be overmolded with one or more gripping surfaces 165 for facilitating gripping and removal of the distal cap 164 from the device. In an exemplary embodiment, the entire exterior surface of the distal cap 164 may be covered by an overmolded gripping surface 165. Corresponding recesses may be provided on the exterior surface of the distal cap 164 to accommodate the gripping surfaces.

In an exemplary embodiment, one or more ridges (that protrude from the exterior surface) and/or one or more grooves or divots (that are depressed into the exterior surface) may be provided at the gripping surfaces 165 on the distal cap 164 to further facilitate gripping and manipulation of the device. The shapes and locations of the ridges and/or grooves may be altered as desired, and any desired number of ridges and/or grooves may be provided. In an exemplary embodiment, the ridges and/or grooves may extend substantially perpendicularly to the longitudinal axis L of the device. In an exemplary embodiment, the gripping surfaces 165 may include textured surfaces to improve the tactile feel and further facilitate firm gripping of the device. In an exemplary embodiment, the distal cap 164 may include one or more protrusions 170a, 170b (shown in FIG. 5) that extend outwardly from the front surface and the back surface of the distal cap 164 to further facilitate gripping of the cap 164.

In an exemplary embodiment, the distal cap 164 may frictionally engage a recessed or stepped portion of the housing in order to be retained in position on the housing when the device is not in use. In an exemplary embodiment, the distal cap 164 may include a boss for locking and/or joining the cap to the housing until the user is ready to perform an injection. Any suitable mating mechanism may be used in accordance with the teachings of exemplary embodiments.

When the proximal terminal end 172, the first body portion 116 and the second body portion 118 are assembled together, they form a tapered tubular structure. Side surfaces of the body portions 116, 118 abutting the gripping surfaces 173 on the proximal terminal end 172 may include one or more recessed or concave portions 122, 124. In an exemplary embodiment, two recessed portions 122, 124 may be provided at opposite sides of the device abutting the firing button 120. The recessed portions allow the hand of the user to be accommodated in a comfortable position when pressing the firing button 120.

A portion of the body portions 116, 118 abutting the recessed portions 122, 124 may be overmolded with one or more gripping surfaces 154, 156 to facilitate holding and manipulation of the device. In an exemplary embodiment, two gripping surfaces 154, 156 may be provided at opposite side surfaces of the device. A first gripping surface 154 may abut a first recessed portion 122, and a second gripping surfaces 156 may abut a second recessed portion 124. Corresponding recesses may be provided on the exterior surface of the first body portion 116 to accommodate the gripping surfaces.

In an exemplary housing for an automatic injection device, a first overmolded gripping region, a second overmolded gripping region and a recessed region abutting the first and second overmolded gripping regions may be provided. The first overmolded gripping region, the second overmolded gripping region and the recessed region may cooperatively provide an ergonomic and comfortable gripping area at which a user may grip the automatic injection device in order to perform an injection.

In this exemplary embodiment, the first overmolded gripping region may be formed by the proximal terminal end 172 having an overmolded outer surface or covering. The second overmolded gripping region may be formed part of the assembly of the first body portion 116 and the second body portion 118 having one or more overmolded gripping surfaces (for example, gripping surfaces 154, 156). In an exemplary embodiment, the second overmolded gripping region may have a substantially tapered tubular structure for providing an ergonomic fit with a user's hand. The recessed region abutting the first and second overmolded gripping regions may be formed by a portion of the assembly of the first body portion 116 and the second body portion 118 that is narrower in width than the first overmolded gripping region and the second overmolded gripping region. In an exemplary embodiment, the recessed region may be provided between the first and second overmolded gripping regions. In an exemplary embodiment, the recessed region may lack any overmolded gripping surfaces.

Figure 3:
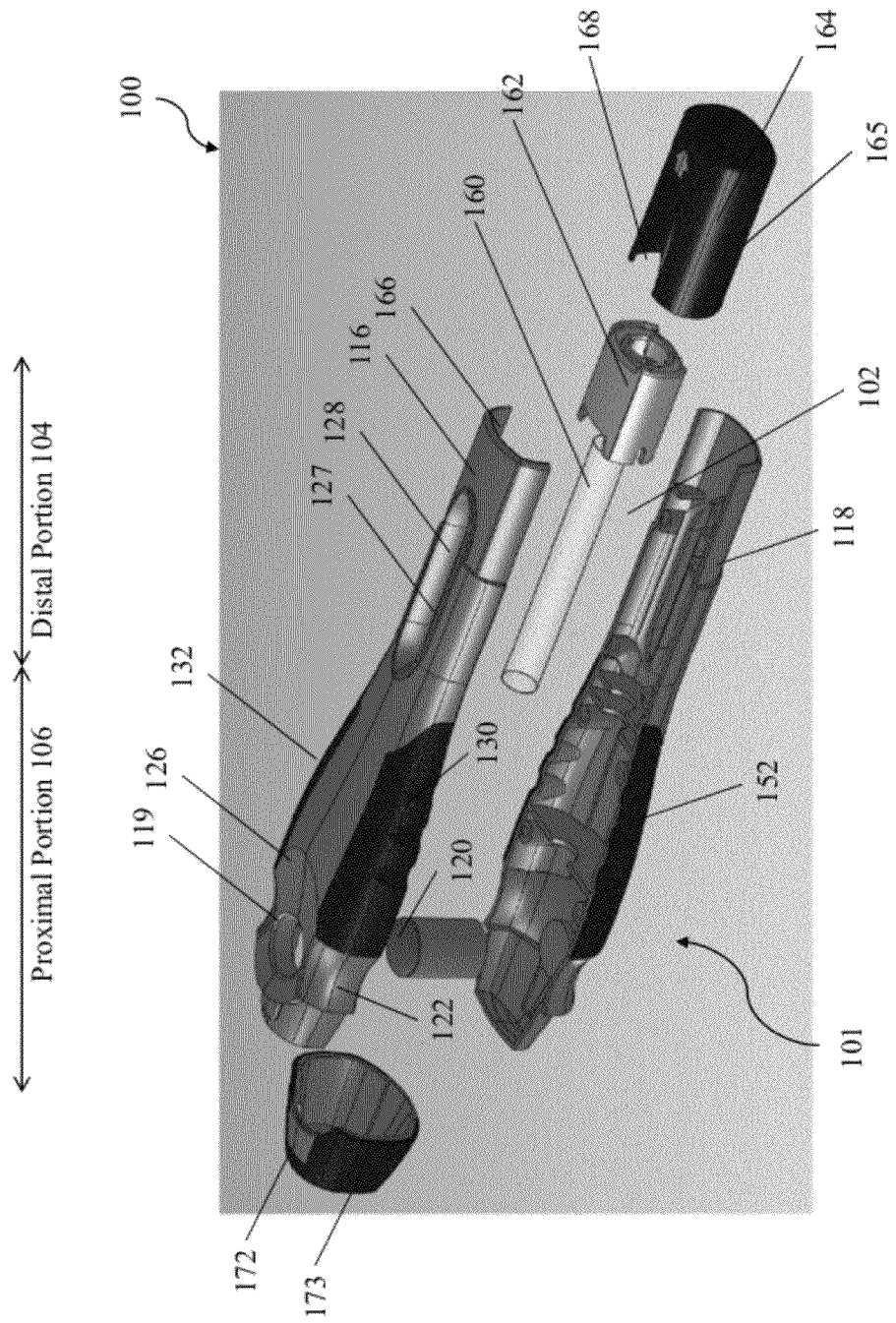
FIG. 3 is a left side exploded perspective view of the exemplary automatic injection device of FIGS. 1 and 2.

FIG. 3 illustrates an exploded view of the exemplary automatic injection device 100 of FIGS. 1 and 2. In an exemplary embodiment, the first body portion 116 may include a substantially planar front surface (extending substantially along the L-H plane) and left and right side surfaces (extending substantially along the L-V plane). The front surface of the first body portion 116 may contiguously and integrally transition to left and right side surfaces of the first body portion 116. The edges at which the front surface transitions to the side surfaces may be sharp, or smooth and rounded in order to maintain a streamlined shape of the device and for ergonomic handling of the device. The front and/or side surfaces of the first body portion 116 may be substantially flat or slightly convex so that the assembled housing ergonomically fits within a user's hand. The front surface may be wider at the proximal portion 106 of the device than at the distal portion 104. One of ordinary skill in the art will recognize that other exemplary shapes are possible for the first body portion 116 of the device.

In an exemplary embodiment, the second body portion 118 may include a substantially planar front surface (extending substantially along the L-H plane) and left and right side surfaces (extending substantially along the L-V plane). The front surface of the second body portion 118 may contiguously and integrally transition to left and right side surfaces of the second body portion 118. The edges at which the front surface transitions to the side surfaces may be sharp, or smooth and rounded in order to maintain a streamlined shape of the device and for ergonomic handling of the device. The front and/or side surfaces of the second body portion 118 may be substantially flat or slightly convex so that the assembled housing ergonomically fits within a user's hand. The front surface may be wider at the proximal portion 106 of the device than at the distal portion 104. One of ordinary skill in the art will recognize that other exemplary shapes are possible for the second body portion 118 of the device.

As illustrated in FIG. 3, the first body portion 116 and the second body portion 118 may be cooperatively engaged to each other along their peripheral edges to enclose and provide a cavity 102 therebetween. The upper and second body portions may be cooperatively engaged to each other using any suitable technique including, but not limited to, bonding, gluing, ultrasonic welding, friction fit, snap fit, interference fit, screws, attachment between corresponding protrusions and recesses, and the like. One of ordinary skill in the art will recognize that, in other exemplary embodiments, the cavity 102 of the device may be enclosed in a single body component or in three or more body components when assembled together.

An exemplary container 160 is preferably slidably positioned in the cavity 102 and is coupled to an injection needle (not shown) at a distal end. The injection needle may be covered by a needle shield 162, for example, a soft needle shield and/or a rigid needle shield. A container advancement mechanism may be provided within the housing to mechanically advance the container 160 within and relative to the housing and to eject the therapeutic agent from the container 160 for performing an injection. The container advancement mechanism may include one or more actuators (e.g., one or more biasing members) that move the container from a sheathed position to a projecting position. When the device is in a pre-injection state, the container 160 may be in a sheathed position, i.e., retracted within the housing. When the device is actuated, the container advancement mechanism may advance the container 160 to a projecting position so that the injection needle projects from a distal end of the housing to allow ejection of the therapeutic agent into a patient's body. The distal end of the housing may include an aperture through which the needle may project.

The cavity 102 within the housing may also accommodate a firing engagement mechanism, for example, the firing button 120. The firing button 120, when actuated by depressing, activates the container advancement mechanism that, in turn, advances the container 160 toward the injection site, drives the injection needle into the injection site and delivers the therapeutic agent into the injection site. In an exemplary embodiment, at least a portion of the exterior surface of the firing button 120 may be overmolded with one or more rubberized gripping surfaces to facilitate pressing of the firing button by a user's finger or hand. In an exemplary embodiment, the entire exterior surface of the firing button may be covered by an overmolded gripping surface. In an exemplary embodiment, the gripping surfaces on the firing button 120 may be colored differently from the non-gripping surfaces to provide a visual affordance to indicate which area of the device should be gripped. For example, the one or more gripping surfaces on the firing button 120 may be green, while all other surfaces on the device may be one or more colors that are not green.

FIG. 3 shows that a front surface of the first body portion 116 may include a first aperture 119 through which the firing button 120 may protrude outside the front surface. An exemplary aperture 119 may be circular to accommodate the firing button 120 with a circular cross-section, although other shapes are possible. The front surface of the first body portion 116 may include a second aperture 127 for accommodating the transparent inspection window 128.

As illustrated in FIG. 3, in an exemplary embodiment, the removable distal cap 164 may frictionally engage a recessed or stepped portion 166 of the housing in order to be retained in position on the housing when the device is not in use.

Figure 4:
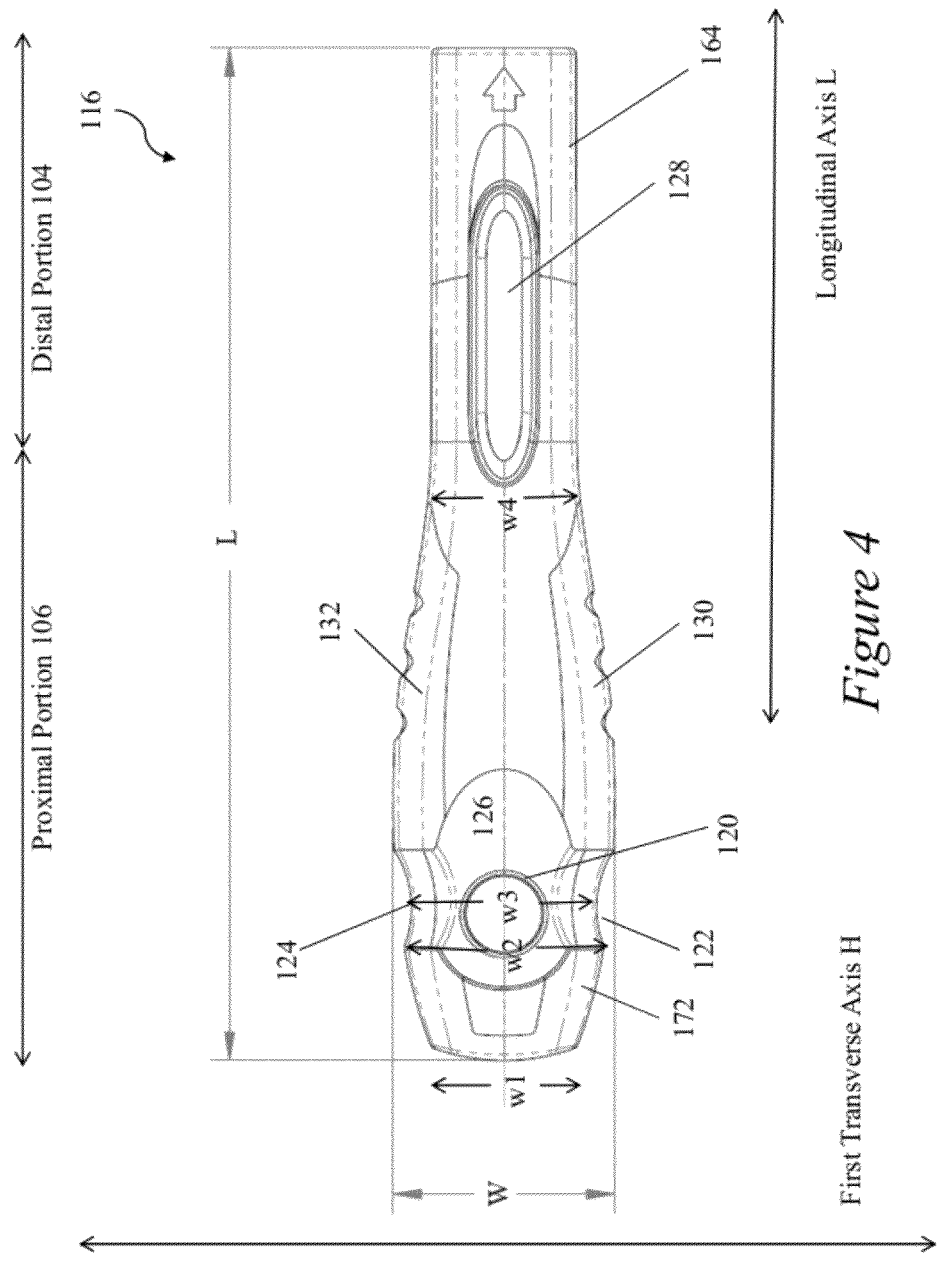
FIG. 4 is a front view of the exemplary automatic injection device of FIGS. 1-3.
Figure 5:
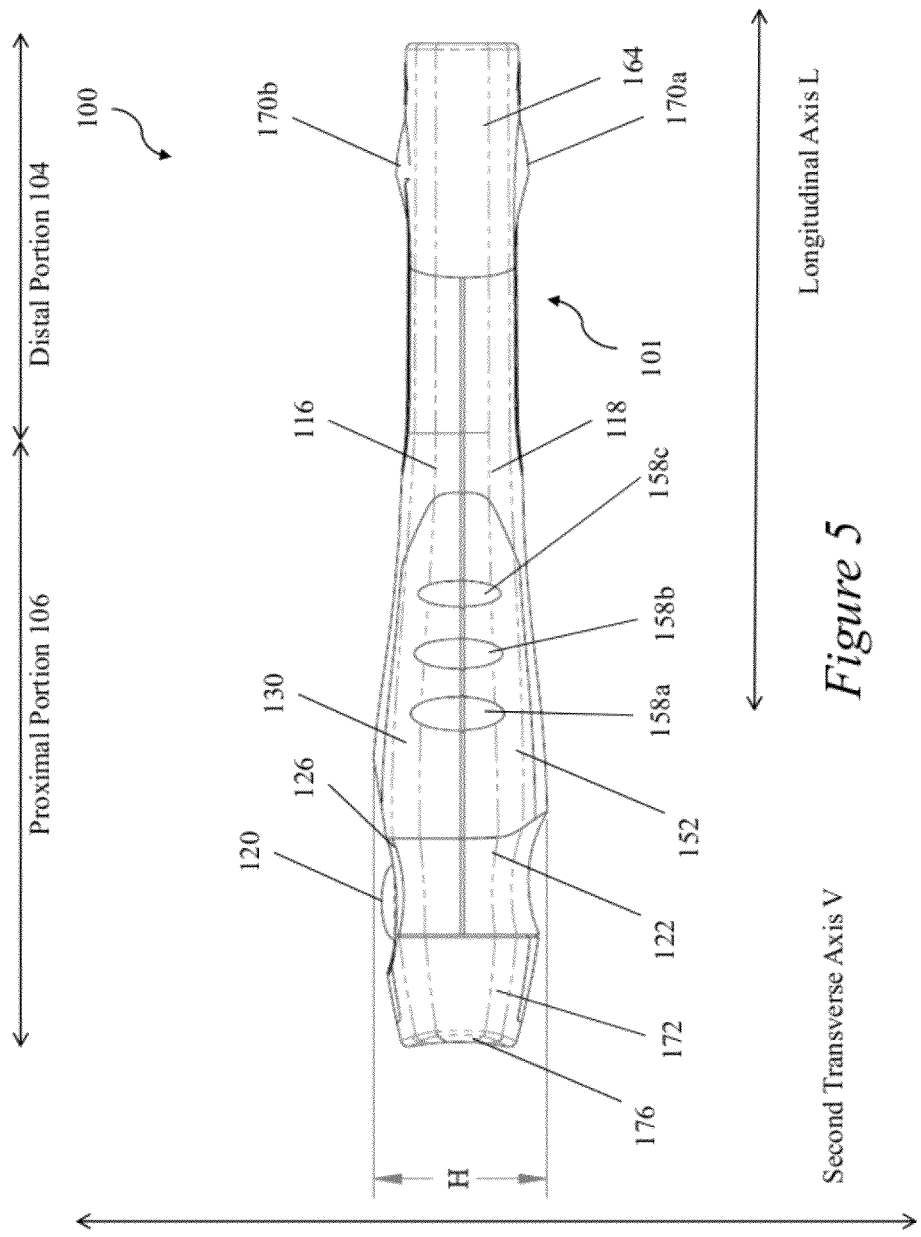
FIG. 5 is a left side view of the exemplary automatic injection device of FIGS. 1-3, the right side view being a mirror image of the left side view.

FIG. 4 illustrates a front surface of the first body portion 116 of the exemplary automatic injection device 100. FIG. 5 illustrates a left side view of the first body portion 116 and the second body portion 118 as assembled in the device 100.

As illustrated in FIG. 4, an exemplary automatic injection device 100 may have a tapered tubular shape with a substantially elongated, elliptical cross-section. The proximal terminal end 172 of the device may have a narrower proximal end (width w1) that broadens slightly and gradually to a larger width (width w2) at the distal end of the proximal terminal end 172. The proximal end of the first body portion 116 abutting the proximal terminal end 172 may include one or more recessed portions 122, 124 at the sides. The recessed portions 122, 124 may create a narrow necked portion (width w3) that is narrower than the adjacent width (width w2) of the proximal terminal end 172. At the distal end of the recessed portions 122, 124, the first body portion 116 may widen to the largest width of the device (width W) and may gradually taper to a narrower width (width w4) near the mid-portion of the device. At the distal portion 104 of the device, the first body portion 116 may have a substantially uniform narrow width (width w4). The second body portion 118 may have a substantially similar shape and configuration as the first body portion 116. As illustrated in FIG. 5, in an exemplary embodiment, the removable distal cap 164 may include one or more protrusions 170a, 170b (shown in FIG. 5) that extend outwardly from the front surface and the back surface of the distal cap 164 to further facilitate gripping of the distal cap.

One of ordinary skill in the art will recognize that other shapes are possible in exemplary automatic injection device 100.

As illustrated in FIGS. 4 and 5, in an exemplary embodiment, a left gripping surface 130 may be provided to partly cover and extend across the left side surface of the first body portion 116, and a right gripping surface 132 may be provided to partly cover and extend across the right side surface of the first body portion 116. In an exemplary embodiment, each gripping surface 130, 132 may be disposed between the firing button 120 and the inspection window 128. One of ordinary skill will recognize that other placements of the gripping surfaces 130, 132 are possible. Similarly, in an exemplary embodiment, a left gripping surface 152 may be provided to partly cover and extend across the left side surface of the second body portion 118, and a right gripping surface 153 may be provided to partly cover and extend across the right side surface of the second body portion 118. When the first and second body portions are assembled, the left gripping surfaces 130, 152 may form a contiguous left gripping surface 154 on the housing, and the right gripping surfaces 132, 153 may form a contiguous right gripping surface 156 on the housing. The left and right contiguous gripping surfaces 154, 156 facilitate reliable and comfortable gripping and manipulation of the device by a user's hand, which markedly and surprisingly improves the user experience of physically weak users, for example, older users and users suffering from rheumatoid arthritis.

In user tests performed using exemplary automatic injection devices, test participants liked the overmolded gripping surfaces on the sides of the device, the ridges on the overmolded gripping surfaces, and the relatively large size and ergonomic shape of the device. Most test participants (58%) strongly preferred the handling and grip of an example automatic injection device of the present invention. Overall, the example device configuration received a high average rating of 8.1 out of 10.0. The overmolded gripping surfaces were the primary factor in the participants' high ratings of the example device for handling and grip. For several usability factors, there was a significant positive correlation between Cochin scores and the example device of the present invention with the overmolded gripping surfaces, which indicates that the example device of the present invention is well-suited for those with hand dysfunction.

One of ordinary skill in the art will recognize that the left and right gripping surfaces may have different sizes, shapes and configurations than the exemplary sizes, shapes and configurations shown in FIGS. 1-8. One of ordinary skill in the art will recognize that more or fewer gripping surfaces may be provided on exemplary automatic injection devices that the exemplary left and right gripping surfaces shown in FIGS. 1-8. One of ordinary skill in the art will also recognize that one or more gripping surfaces may be positioned on exemplary automatic injection devices in positions other than the exemplary positions shown in FIGS. 1-8. Further, one of ordinary skill in the art will recognize that the outline of each gripping surface may have a smooth, rounded, streamlined configuration in some exemplary embodiments.

The overmolded gripping surfaces provided in exemplary embodiments may be formed of any suitable material that provides a first soft and high-friction touch perception to a user, as compared to the portions of the device that lack an overmolded gripping surface which provide a second hard and low-friction touch perception to a user. The difference in the sensory perceptions provides a touch affordance to a user, indicating that the device is to be gripped at regions provided with the overmolded gripping surfaces.

In an exemplary embodiment, the overmolded gripping surfaces may be formed of a first type of material having a soft, high-friction touch perception to a user, while the portions of the device lacking overmolded gripping surfaces may be formed of a second type of material having a harder, lower-friction touch perception to a user. In an exemplary embodiment, the overmolded gripping surfaces may be formed of a first material with a lower hardness, while the non-gripping surfaces may be formed of a second material with a higher hardness.

For example, the non-gripping surfaces may be formed of any rigid thermoplastic material or rigid substrate suitable for use in a medical device application and suitable for providing a hard, low-friction touch perception to the user. Rigid thermoplastics can include materials such as polypropylene (PP), polyethylene (PE), polystyrene (PS), high impact polystyrene (HIPS), polycarbonate (PC), acrynitrile-butadiene-styrene (ABS), poly(ethylene terephthalate) (PET), polyamide (PA), PC/ABS blend and PPO/PS blends.

Exemplary overmolded gripping surfaces may be formed of materials having any suitable material grade and hardness for providing a soft, high-friction touch perception to the user. Exemplary overmolded gripping surface materials may include, but are not limited to, rubber (for example, having a durometer of 50 A in one embodiment), thermoplastic elastomers (TPEs), thermoplastic vulcanizate (TPV), and the like. Exemplary thermoplastic elastomers that may be used to form exemplary overmolded gripping surfaces include, but are not limited to, TPEs from KRAIBURG, the Dynaflex™ TPE from PolyOne, the Versaflex™ TPE from PolyOne, the Versollan™ TPE from PolyOne, the OnFlex™ TPE from Polyone, and the like. Exemplary thermoplastic vulcanizates that may be used to form exemplary overmolded gripping surfaces include, but are not limited to, the Santoprene™ thermoplastic from ExxonMobil and the like.

In an exemplary embodiment, the overmolded gripping surfaces may be colored differently from the non-gripping surfaces to provide a visual affordance to indicate which area of the device should be gripped. For example, the left and right overmolded gripping surfaces may be maroon in color while the non-gripping surfaces on the housing may be grey in color.

Figure 6A:
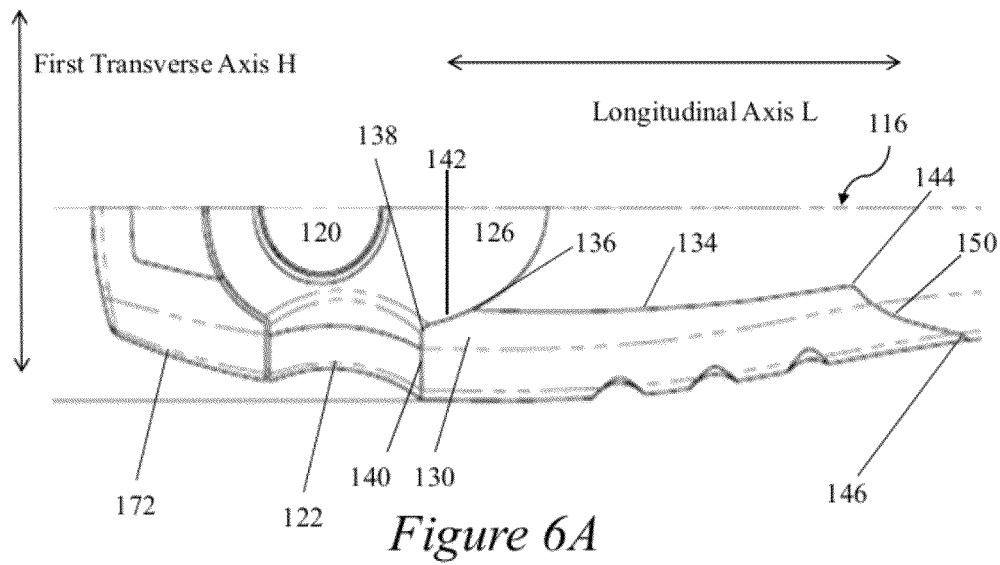
FIG. 6A is a front close-up view of an exemplary left gripping surface provided on a first body portion of the device of FIGS. 1-3.
Figure 6B:
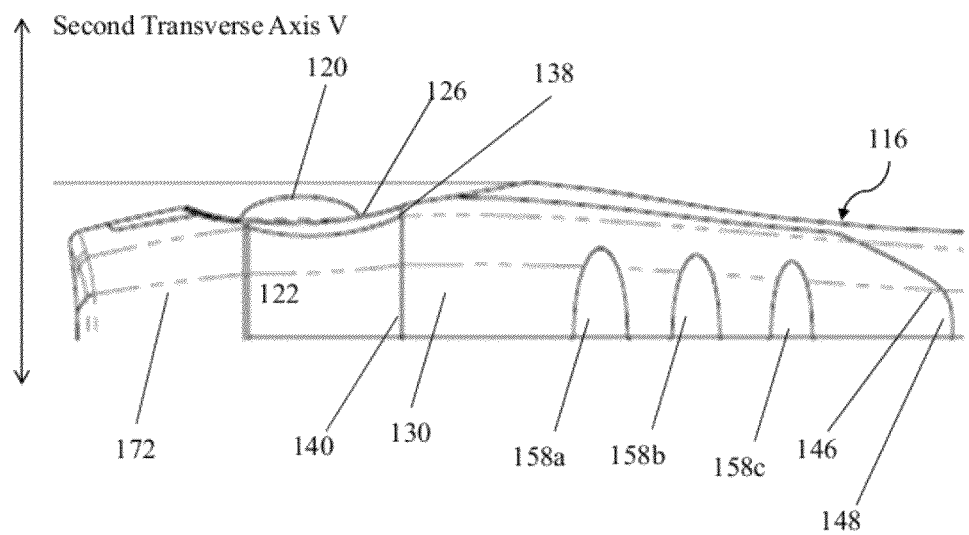
FIG. 6B is a left side close-up view of the exemplary left gripping surface of FIG. 6A.

As illustrated in FIG. 5, in an exemplary embodiment, one or more ridges (that protrude from the exterior surface) and/or one or more grooves or divots (that are depressed with the exterior surface) 158a, 158b, 158c (as illustrated in FIGS. 5 and 6B) may be provided at the left overmolded gripping surface 154 and/or the right overmolded gripping surface 156 to further facilitate gripping and manipulation of the device. The shapes and locations of the ridges and/or grooves may be altered as desired, and any desired number of ridges and/or grooves may be provided. In an exemplary embodiment, the ridges and/or grooves may extend substantially perpendicularly to the longitudinal axis L of the device. In an exemplary embodiment, the overmolded gripping surfaces may include textured surfaces to improve the tactile feel and further facilitate firm gripping of the device.

FIG. 6A is a front close-up view of an exemplary left overmolded gripping surface 130 provided on a first body portion 116 of the device 100 of FIG. 1. FIG. 6B is a left side close-up view of the exemplary left overmolded gripping surface 130 of FIG. 6A. The right overmolded gripping surface 132 of the first body portion 116, the left overmolded gripping surface 152 of the second body portion 118, and the right overmolded gripping surface 153 of the second body portion 118 may be similar in structure and configuration.

Referring to FIGS. 6A and 6B, the left overmolded gripping surface 130 may have a first longitudinal side 134 that extends on the front surface of the first body portion 116 substantially along the longitudinal axis L. In an exemplary embodiment, the first longitudinal side 134 of the left overmolded gripping surface 130 may be substantially linear, while in another exemplary embodiment, the first longitudinal side 134 may be slightly concave or convex. A proximal end 136 of the first longitudinal side 134 may extend toward and connect with an end 138 of a first horizontal side 140 of the left overmolded gripping surface 130. The first horizontal side 140 may extend across the left side surface of the first body portion 116 substantially along the second transverse axis V, ending at the peripheral edge of the first body portion 116.

In an exemplary embodiment, a connecting side 142 extending between ends 136, 138 may connect the first longitudinal side 134 to the first horizontal side 140. In an exemplary embodiment, the first horizontal side 140 may include a beveled edge extending to the first longitudinal side 134 at an angle to both longitudinal axis L and the first transverse axis H.

In an exemplary embodiment, the first longitudinal side 134 of the left overmolded gripping surface 130 may be substantially longer than the first horizontal side 140. An exemplary ratio of the length of the first longitudinal side 134 to the length of the first horizontal side 140 may include, but is not limited to, about 2:1, 2.5:1, 3:1, 3.5:1, 4:1, 4.5:1, 5:1, all intermediate ratios, and the like.

A distal end 144 of the first longitudinal side 134 may extend toward and connect with an end 146 of a second horizontal side 148 of the left overmolded gripping surface 130. In an exemplary embodiment, a connecting side 150 extending between the ends 144, 146 may connect the first longitudinal side 134 to the second horizontal side 148. In an exemplary embodiment, the connecting side 150 may have a length greater than that of the connecting side 142. In exemplary embodiments, a ratio of the length of the connecting side 150 to the length of the connecting side 142 may include, but is not limited to, 1.5:1, 1.75:1, 2:1, 2.25:1, 2.5:1, 2.75:1, 3:1, 3.25:1, 3.5:1, 3.75:1, 4:1, all intermediate ratios, and the like, but is not limited to these exemplary ratios. The second horizontal side 148 may extend across the left side surface of the first body portion 116 substantially along the second transverse axis V, ending at the peripheral edge of the first body portion 116.

In an exemplary embodiment, the first longitudinal side 134 may be substantially longer than either the first horizontal side 140 or the second horizontal side 148. An exemplary ratio of the length of the first longitudinal side 134 to the length of either horizontal side may include, but is not limited to, about 2:1, 2.5:1, 3:1, 3.5:1, 4:1, 4.5:1, 5:1, 5.5:1, 6:1, 6.5:1, 7:1, all intermediate ratios, and the like.

Figure 7:
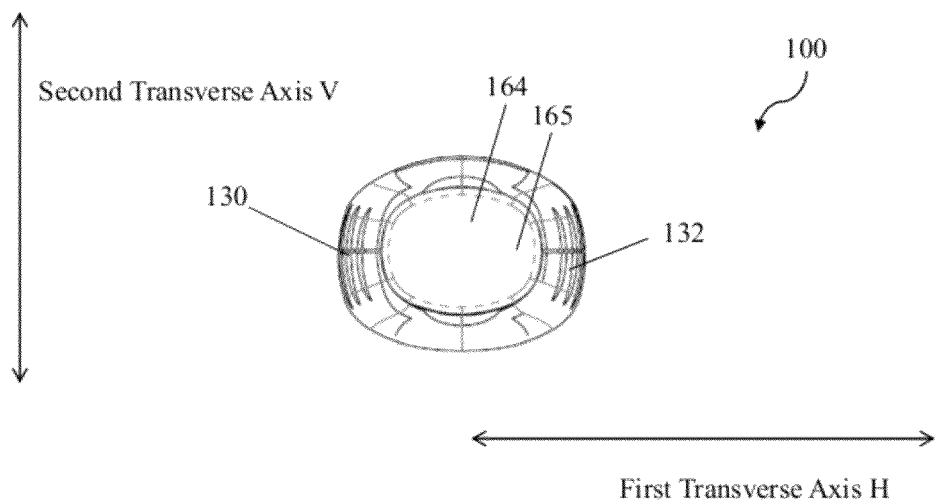
FIG. 7 is a bottom view of an exemplary removable distal cap of the exemplary automatic injection device of FIGS. 1-3.

FIG. 7 is a bottom view of an exemplary removable distal cap 164 showing the overmolded gripping surface 165. The overmolded gripping surfaces 165 may be formed of any suitable material that provides first a soft and high-friction touch perception to a user, as compared to the portions of the device that lack an overmolded gripping surface which provide a hard and low-friction touch perception to a user. The difference in the sensory perceptions provides a touch affordance to a user, indicating that the device is to be gripped at regions provided with the overmolded gripping surfaces.

In an exemplary embodiment, the overmolded gripping surfaces may be formed of a first type of material having a soft, high-friction touch perception, while the non-gripping surfaces are formed of a second type of material having a harder, lower-friction touch perception. Exemplary overmolded gripping surfaces 165 may be formed of materials having any suitable material grade and hardness for providing a soft, high-friction touch perception to the user. Exemplary overmolded gripping surface materials may include, but are not limited to, rubber (for example, having a durometer of 50 A in one embodiment), thermoplastic elastomers (TPEs), thermoplastic vulcanizate (TPV), and the like. Exemplary thermoplastic elastomers that may be used to form exemplary overmolded gripping surfaces include, but are not limited to, TPEs from KRAIBURG, the Dynaflex™ TPE from PolyOne, the Versaflex™ TPE from PolyOne, the Versollan™ TPE from PolyOne, the OnFlex™ TPE from Polyone, and the like. Exemplary thermoplastic vulcanizates that may be used to form exemplary overmolded gripping surfaces include, but are not limited to, the Santoprene™ thermoplastic from ExxonMobil and the like. In an exemplary embodiment, the overmolded gripping surfaces 165 may be colored differently from the non-gripping surfaces to provide a visual affordance to indicate which area of the device should be gripped. For example, the one or more overmolded gripping surfaces 165 on the distal cap 164 may be maroon in color while the non-gripping surfaces on the housing may be grey in color.

Figure 8:
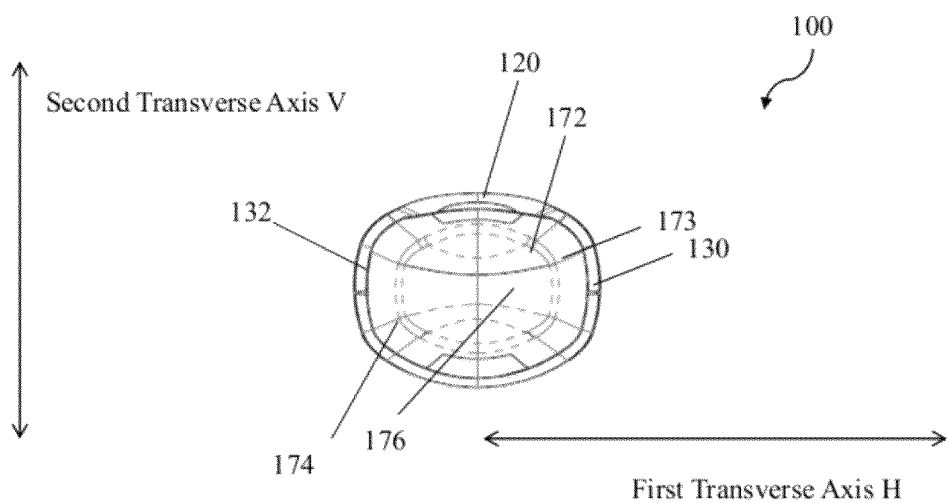
FIG. 8 is a top view of an exemplary proximal terminal end of the exemplary automatic injection device of FIGS. 1-3.

FIG. 8 is a top view of an exemplary proximal terminal end 172 for covering the proximal end of the housing. In an exemplary embodiment, the exterior surface of the proximal terminal end 172 may lack any overmolded gripping surfaces. In other exemplary embodiments, at least part of the exterior surface of the proximal terminal end 172 may be overmolded with one or more gripping surfaces 173 to facilitate gripping of the proximal portion of the device. In an exemplary embodiment, the entire exterior surface of the proximal terminal end 172 may be covered by an overmolded gripping surface 173.

The overmolded gripping surfaces 173 may be formed of any suitable material that provides a first soft and high-friction touch perception to a user, as compared to the portions of the device that lack an overmolded gripping surface which provide a second soft and low-friction touch perception to a user. The difference in the sensory perceptions provides a touch affordance to a user, indicating that the device is to be gripped at regions provided with the overmolded gripping surfaces.

In an exemplary embodiment, the overmolded gripping surfaces 173 may be formed of a first type of material having a soft, high-friction touch perception, while the non-gripping surfaces are formed of a second type of material having a harder, lower-friction touch perception. Exemplary overmolded gripping surfaces 173 may be formed of materials having any suitable material grade and hardness for providing a soft, high-friction touch perception to the user. Exemplary overmolded gripping surface materials may include, but are not limited to, rubber (for example, having a durometer of 50 A in one embodiment), thermoplastic elastomers (TPEs), thermoplastic vulcanizate (TPV), and the like. Exemplary thermoplastic elastomers that may be used to form exemplary overmolded gripping surfaces include, but are not limited to, TPEs from KRAIBURG, the Dynaflex™ TPE from PolyOne, the Versaflex™ TPE from PolyOne, the Versollan™ TPE from PolyOne, the OnFlex™ TPE from Polyone, and the like. Exemplary thermoplastic vulcanizates that may be used to form exemplary overmolded gripping surfaces include, but are not limited to, the Santoprene™ thermoplastic from ExxonMobil and the like. In an exemplary embodiment, the overmolded gripping surfaces 173 may be colored differently from the non-gripping surfaces to provide a visual affordance to indicate which area of the device should be gripped. For example, the one or more overmolded gripping surfaces 173 on the proximal terminal end 172 may be maroon in color while the non-gripping surfaces on the housing may be grey in color.

In an exemplary embodiment, one or more ridges (that protrude from the exterior surface) and/or one or more grooves or divots (that are depressed into the exterior surface) may be provided on the exterior surface of the proximal terminal end 172 to further facilitate gripping of the proximal portion of the device. The shapes and locations of the ridges and/or grooves may be altered as desired, and any desired number of ridges and/or grooves may be provided. In an exemplary embodiment, the overmolded gripping surfaces 173 may include textured surfaces to improve the tactile feel and further facilitate firm gripping of the device. In an exemplary embodiment, a wrap-around groove 174 may be provided around the circumference of the proximal terminal end 172 and a concave or recessed surface 176 may be provided at the top of the proximal terminal end 172 in order to orient and guide a user's hand and fingers to the device. For example, the concave or recessed surface 176 may accommodate a finger on the surface 176 while the user is performing an injection using the device.

In some exemplary embodiments, the housing 101, the removable distal cap 164 and/or the proximal terminal end 172 of the device 100 may further include graphics, symbols and/or numbers to facilitate use of the automatic injection device. For example, the distal cap 164 may include a depiction of an arrow on an outer surface pointing towards the distal end of the device to indicate how the device should be held relative to the patient (i.e., with the distal end adjacent to the injection site). One of ordinary skill in the art will recognize that the automatic injection device may have any suitable graphics, symbols and/or numbers to facilitate patient instruction, or the automatic injection device may omit such graphics, symbols and/or numbers.

Figure 9:
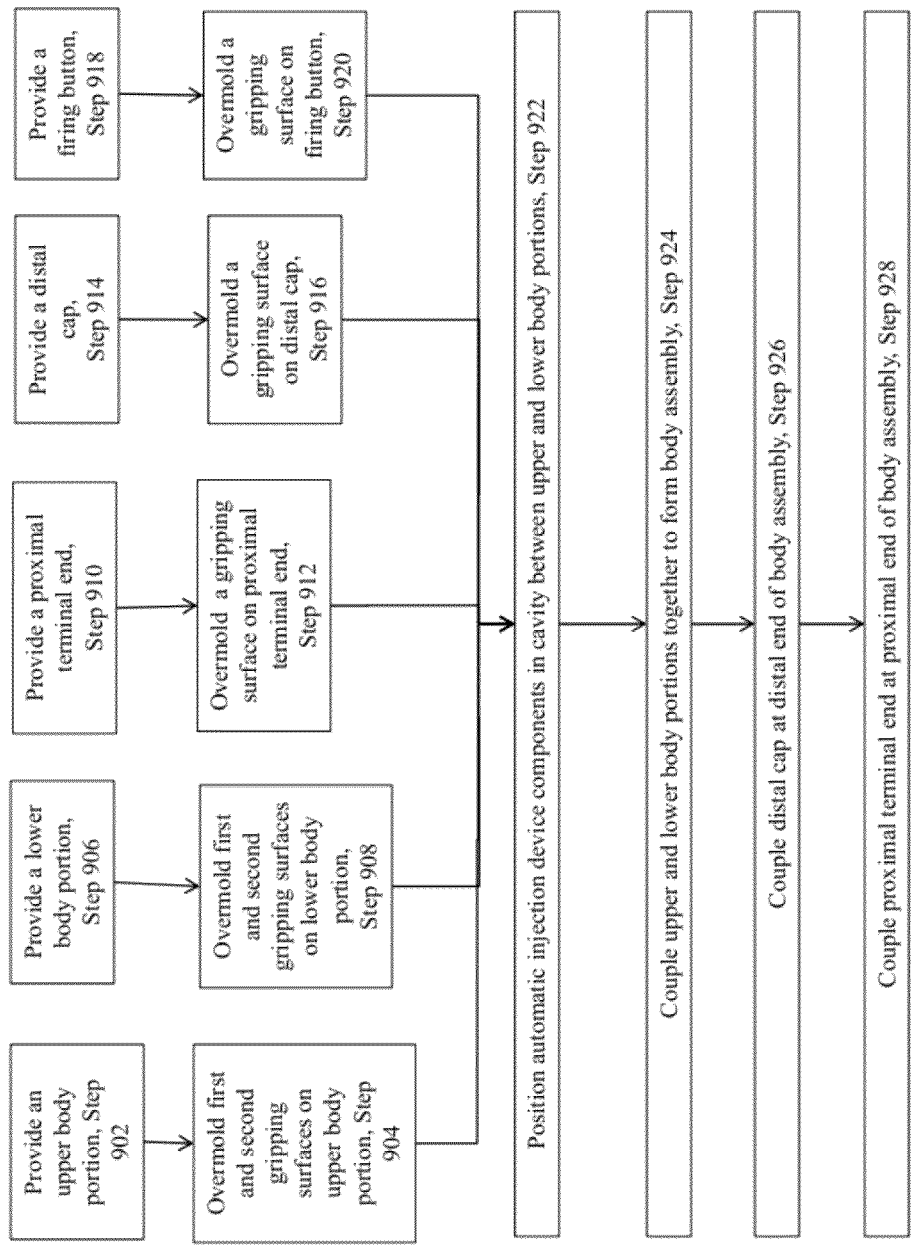
FIG. 9 is a flowchart of an exemplary method for forming an exemplary automatic injection device.

FIG. 9 is a flowchart of an exemplary method of assembling an exemplary automatic injection device. In an exemplary embodiment, a housing of an exemplary automatic injection device may be provided in two or more separate housing components (for example, first and second body portion) that may be coupled together during assembly of the device.

In step 902, a first body portion of the housing is provided or formed. In step 904, one or more gripping surfaces are overmolded on corresponding recesses on the exterior surface of the first body portion to facilitate gripping and manipulation of the device during an injection.

In step 906, a second body portion of the housing is provided or formed. In step 908, one or more gripping surfaces are overmolded on corresponding recesses on the exterior surface of the second body portion to facilitate gripping and manipulation of the device during an injection.

In step 910, a proximal terminal end of the housing is provided or formed. In step 912, one or more gripping surfaces are overmolded on corresponding recesses on the exterior surface of the proximal terminal end to facilitate gripping and manipulation of the device.

In step 914, a removable distal cap of the housing is provided or formed. In step 916, one or more gripping surfaces are overmolded on corresponding recesses on the exterior surface of the distal cap to facilitate removal of the distal cap before performing an injection.

In step 918, a firing button of the housing is provided or formed. In step 920, one or more gripping surfaces are overmolded on the exterior surface of the firing button to facilitate activation of the firing button to perform an injection.

In step 922, one or more internal components of the automatic injection device may be positioned in a cavity defined between the upper and second body portions. Exemplary device components may include, but are not limited to, a container (e.g., a syringe) pre-filled with a therapeutic agent for injecting into a patient, an injection needle coupled to a distal end of the container, a container advancement mechanism for advancing the container within and relative to the housing toward the injection site and for ejecting the therapeutic agent from the container during an injection, a firing button for activating the container advancement mechanism, and the like.

In step 924, the upper and second body portions may be cooperatively engaged to form a body assembly that encloses and holds the internal components within the cavity. In an exemplary embodiment, the body portions may be coupled at their peripheral edges. Any suitable coupling or joining may be used in step 924 including, but not limited to, bonding, gluing, ultrasonic welding, friction fit, snap fit, interference fit, screws, corresponding protrusions and recesses, and the like.

In step 926, the removable distal cap may be removably coupled at a distal end of the body assembly to cover an injection needle or a needle shield that, in turn, covers the injection needle.

In step 928, the proximal terminal end may be coupled at a proximal end of the body assembly.

Any suitable fabrication technique may be used to form any of the device components including, but not limited to, injection molding. The device components may be formed of any suitable material including, but not limited to, plastics, thermoplastics, polycarbonates, metals, and the like.

It is noted that the order of the steps discussed herein may be altered as desired and that other fabrication steps/techniques are possible and are considered within the spirit and scope of the present invention.

Automatic Injection Device User Tests

Forty-four test participants were recruited to test both the exemplary automatic injection devices having overmolded gripping surfaces of the present invention and four alternate automatic injection devices without such gripping surfaces. A majority of the participants were suffering from rheumatoid arthritis (RA) at the time of the test. The participants were diagnosed with RA from 1 to 40 years ago, with an average age of diagnosis of 9 years ago. Four participants were suffering from Crohn's disease at the time of the test.

Test Procedure

Each test participant tested the different exemplary automatic injection device configurations. In particular, in an example device use phase, each test participant performed a simulated injection (i.e., an injection with clipped needles and no medicament) using the devices. After he/she performed a simulated injection, each test participant was asked a series of follow-up questions designed to assess the participant's approval of the form and function of the devices. These questions included questions on, for example, the size, shape, ease of handling, comfort of holding, overall user experience, and the like.

Device Handling and Gripping

Upon performing simulated injections using the different device configurations, test participants were asked to provide feedback and comparative ratings on handling and grip, overall ease of use, and comfort in performing the injection steps. All device configurations were rated on a scale of 1 (very negative) to 10 (very positive).

Most test participants (58%) strongly preferred the handling and grip of the example device configuration of the present invention, compared to four alternate device configurations that did not include overmolded gripping surfaces. Test participants particularly liked the rubberized overmolded grips on the side of the example device and its relatively large size, which made the example device easy and comfortable to hold. The rubberized overmolded grips were the primary factor in participants' high ratings of the example device configuration for handling and grip as taught herein.

Furthermore, a correlation analysis was performed on hand dysfunction using the Cochin hand disability scale with the ratings provided for certain usability factors: handling and gripping, ease of use, ease of starting and performing an injection, comfort of performing injection, acceptability and overall preference. For several usability factors, there was a significant positive correlation between Cochin scores and the example device configuration of the present invention, which indicates that this example device configuration is well-suited for those with hand dysfunction.

Comfort of Device Holding and Use

Upon performing simulated injections in the example device use phase, test participants were asked to rate the comfort of holding the example device configuration of the present invention and four alternate device configurations that did not include any overmolded gripping surfaces. Test participants rated each device configuration on a scale from 1 (very low confidence) to 7 (very high confidence). Most test participants favored the example device configuration of the present invention for comfort in performing injection steps, with 45% rating it the highest.

Ease of Device Use and Handling

Upon initial exposure to the example device and before receiving instructions or a demonstration on use, test participants were asked about the perceived ease of use of the example device configuration of the present invention and four alternate device configurations that did not include any overmolded gripping surfaces. Test participants rated each device configuration on a scale from 1 (very difficult) to 7 (very easy). All of the device configurations received high ratings for their perceived ease of use.

Upon performing simulated injections in the actual device use phase, test participants were asked to rate the ease of handling each device configuration. Test participants rated each device configuration on a scale from 1 (very low confidence) to 7 (very high confidence). Furthermore, upon performing simulated injections using the device configuration in the third actual device use phase, test participants were also asked to rate the configurations on their overall ease of use on a scale of 1 (very difficult) to 10 (very easy).

Most test participants (42%) found the example device configuration of the present invention easiest to use compared to four alternate device configurations that did not include overmolded gripping surfaces. Overall, the example device configuration of the present invention received a high average rating of 7.97 out of 10.0.

Device Size

Upon performing simulated injections in the example device use phase, test participants were asked to rate the overall size of the example device configuration of the present invention and four alternate device configurations that did not include any overmolded gripping surfaces on a scale of 1 (very low confidence) to 7 (very high confidence). All of the device configurations generally received positive ratings for their overall shape. In general, test participants who struggled to form a tight fist preferred larger devices. The example device configuration of the present invention generally received the highest ratings.

Device Shape

Upon performing simulated injections in the actual device use phase, test participants were asked to rate the overall shape of the example device configuration of the present invention and four alternate device configurations that did not include any overmolded gripping surfaces on a scale of 1 (very low confidence) to 7 (very high confidence).

All of the device configurations generally received positive ratings for their overall size. In general, test participants who struggled to form a tight fist preferred larger devices. With respect to the example device configuration of the present invention, many participants found that the shape fit nicely in their hand.

III. INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

IV. EQUIVALENTS

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

What is claimed is:

1. An automatic injection device, comprising:
    a housing enclosing a cavity for accommodating a container, a proximal portion of the housing having a tapered tubular structure with a substantially oval cross-section;
    a first overmolded gripping surface extending longitudinally along a portion of the housing on a first exterior surface of the housing;
    a second overmolded gripping surface extending longitudinally along a portion of the housing on a second exterior surface of the housing, the first exterior surface and the second exterior surface located on opposing sides of the housing;
    a first concave portion disposed in the first exterior surface of the housing between the first overmolded gripping surface and a proximal terminal end of the housing; and
    a second concave portion disposed in the second exterior surface of the housing between the second overmolded gripping surface and the proximal terminal end of the housing.

2. The automatic injection device of claim 1, wherein the first and second overmolded gripping surfaces on the housing include one or more grooves or ridges for facilitating gripping and manipulation of the automatic injection device.

3. The automatic injection device of claim 1, wherein the first and second overmolded gripping surfaces on the housing are formed of a first material having a first touch perception, and non-gripping surfaces on the housing are formed of a second material having a second touch perception.

4. The automatic injection device of claim 1, wherein the first and second overmolded gripping surfaces on the housing are formed of a first material having a first hardness, and non-gripping surfaces on the housing are formed of a second material having a second, higher hardness.

5. The automatic injection device of claim 1, wherein the first and second overmolded gripping surfaces on the housing have a different color than non-gripping surfaces on the housing.

6. The automatic injection device of claim 1, further comprising:
a removable distal cap for protectively covering an injection needle couplable to the container, an exterior surface of the distal cap including an overmolded gripping surface for facilitating gripping and removal of the distal cap.

7. The automatic injection device of claim 6, wherein the exterior surface of the distal cap includes one or more grooves or ridges for facilitating gripping and removal of the distal cap.

8. The automatic injection device of claim 1, further comprising:
a firing button protruding from an aperture in the housing and including an overmolded contact surface for facilitating actuation of the firing button by a user.

9. The automatic injection device of claim 8, wherein the firing button is positioned along a transverse axis perpendicular to a longitudinal axis of the device.

10. The automatic injection device of claim 9, further comprising:
a recessed surface provided adjacent to the firing button.

11. The automatic injection device of claim 10, wherein the recessed surface is provided surrounding the firing button.

12. The automatic injection device of claim 1, further comprising:
a proximal terminal end for covering a proximal end of the automatic injection device, the proximal terminal end having an overmolded exterior surface.

13. The automatic injection device of claim 12, wherein a top surface of the proximal terminal end includes a recessed surface for directing and facilitating gripping of the automatic injection device.

14. The automatic injection device of claim 1, further comprising:
a transparent inspection window disposed in the housing to allow inspection of the contents of the container.

15. The automatic injection device of claim 14, wherein, at the end of an injection, the inspection window is filled with a visual indicator.

16. The automatic injection device of claim 1, wherein the proximal portion of the device has a shape in which a front face and an opposite back face are planar and in which first and second side faces are convex, for ergonomic and reliable gripping of the proximal portion by a user's hand.

17. The automatic injection device of claim 16, wherein the first and second overmolded gripping surfaces are disposed at the proximal portion of the device and extend across portions of the first and second side faces.

18. The automatic injection device of claim 1, wherein the housing comprises a plurality of housing components cooperatively engaged to define the cavity therein.

19. The automatic injection device of claim 1, wherein the container holds a dose of a TNF inhibitor.

20. The automatic injection device of claim 19, wherein the TNF inhibitor is adalimumab.

21. The automatic injection device of claim 1, wherein a width of the housing at the proximal portion of the housing is larger than a distal portion of the housing.

22. A method for assembling an automatic injection device, the method comprising:
providing a housing enclosing a cavity for accommodating a container, a proximal portion of the housing having a tapered tubular structure with a substantially oval cross-section;
overmolding, on the housing, a first gripping surface extending longitudinally along a portion of the housing on a first exterior surface of the housing;
overmolding, on the housing, a second gripping surface extending longitudinally along a portion of the housing on a second exterior surface of the housing opposite to the first exterior surface;
providing a first concave portion disposed in the first exterior surface of the housing between the first overmolded gripping surface and a proximal terminal end of the housing; and
providing a second concave portion disposed in the second exterior surface of the housing between the second overmolded gripping surface and the proximal terminal end of the housing.

23. The method of claim 22, wherein the first and second gripping surfaces on the housing include one or more grooves or ridges for facilitating gripping and manipulation of the automatic injection device.

24. The method of claim 22, wherein the first and second gripping surfaces on the housing are formed of a first material having a first touch perception, and non-gripping surfaces on the housing are formed of a second material having a second touch perception.

25. The method of claim 22, wherein the first and second gripping surfaces on the housing are formed of a first material having a first hardness, and non-gripping surfaces on the housing are formed of a second material having a second, higher hardness.

26. The method of claim 22, further comprising:
overmolding a gripping surface on an exterior surface of a distal cap to facilitate gripping and removal of the distal cap; and
coupling the distal cap to a distal end of the housing for protectively covering an injection needle.

27. The method of claim 26, wherein the exterior surface of the distal cap includes one or more grooves or ridges for facilitating gripping and removal of the distal cap.

28. The method of claim 22, further comprising:
overmolding a gripping surface on a firing button to facilitate activation of the firing button; and
providing the firing button within the cavity so that part of the firing button protrudes from an aperture in the housing.

29. The method of claim 28, wherein the firing button is positioned along a transverse axis perpendicular to a longitudinal axis of the device.

30. The method of claim 28, further comprising:
forming a recessed surface abutting the firing button.

31. The method of claim 30, wherein the recessed surface is provided surrounding the firing button.

32. The method of claim 22, further comprising:
overmolding a gripping surface on an exterior surface of a proximal terminal end; and
coupling the proximal terminal end to a proximal end of the housing.

33. The method of claim 32, wherein a top surface of the proximal terminal end includes a recessed surface for facilitating gripping of the automatic injection device.

34. An automatic injection device, comprising:
- a housing enclosing a cavity for accommodating a container, the housing comprising:
  - a first overmolded gripping region,
  - a second overmolded gripping region, and
  - a recessed region between and in contact with both the first and second overmolded gripping regions.

35. The automatic injection device of claim 34, wherein a width of the housing at the recessed region is smaller than a width of the housing at the first overmolded gripping region and a width of the housing at the second overmolded gripping region.

36. The automatic injection device of claim 34, wherein the recessed region of the housing lacks a gripping surface.

37. The automatic injection device of claim 34, wherein the first overmolded gripping region is formed by a proximal terminal end of the housing having an exterior surface that is overmolded with a gripping surface.

38. The automatic injection device of claim 34, wherein the second overmolded gripping region of the housing has a tapered tubular structure.

* * * * *